(12) United States Patent
Andersson

(10) Patent No.: US 8,497,352 B2
(45) Date of Patent: Jul. 30, 2013

(54) USE OF WNT5-α PEPTIDE DERIVATES FOR THE TREATMENT OF MELANOMA AND GASTRIC CANCER

(75) Inventor: Tommy Andersson, Malmö (SE)

(73) Assignee: Wntresearch AB, Lund (SE)

( * ) Notice: Subject to any disclaimer, the term of this patent is extended or adjusted under 35 U.S.C. 154(b) by 0 days.

(21) Appl. No.: 13/058,036

(22) PCT Filed: Aug. 13, 2009

(86) PCT No.: PCT/SE2009/050935
§ 371 (c)(1),
(2), (4) Date: Feb. 10, 2011

(87) PCT Pub. No.: WO2010/019103
PCT Pub. Date: Feb. 18, 2010

(65) Prior Publication Data
US 2012/0010151 A1    Jan. 12, 2012

(30) Foreign Application Priority Data
Aug. 13, 2008 (SE) .................................. 0801791

(51) Int. Cl.
  *C07K 7/04* (2006.01)
  *C07K 7/06* (2006.01)
  *C07K 7/08* (2006.01)
  *A61K 38/04* (2006.01)
  *A61P 35/00* (2006.01)

(52) U.S. Cl.
  USPC ......................................... 530/350; 514/19.3

(58) Field of Classification Search
  None
  See application file for complete search history.

(56) References Cited

U.S. PATENT DOCUMENTS

| 4,840,967 A * | 6/1989 | Beeley et al. .................. 514/466 |
| 7,238,709 B2 * | 7/2007 | Mammen et al. ............. 514/317 |
| 7,247,426 B2 | 7/2007 | Yakhini et al. |

FOREIGN PATENT DOCUMENTS

| WO | 98/23730 A1 | 6/1998 |
| WO | 2004/030615 A2 | 4/2004 |
| WO | 2006/130082 A1 | 12/2006 |
| WO | 2009/134204 A1 | 11/2009 |

OTHER PUBLICATIONS

Zips et al., In vitro and in vivo evaluation of new anticancer drugs, In Vivo, 19, 1-8, 2005.*
Henrik Andersen, et al; "Protease-activated receptor 1 is the primary mediator of thrombin-stimulated platelet procoagulant activity", Proc Natl. Acad. Sci. USA; vol. 96, pp. 11189-11103, Sep. 1999, Biochemistry.
M. Bittner, et al; "Molecular classification of cutaneous malignant melanoma by gene expression profiling", Nature, vol. 406, Aug. 3, 3000; pp. 536-540.
Etienne Blanc et al; "Low expression of Wnt-5a gene is associated with high-risk neuroblastoma", Oncogene, vol. 24, Issue 7, Feb. 10, 2005, pp. 1277-1283.
Janna Dejmek, et al; "Wnt-54a Protein Expression in Primary Dukes B Colon Cancers Identifies a Subgroup of Patient with Good Prognosis", Cancer Res 2005; 65; (20z0. Oct. 15, 2005, pp. 9142-9146; www.aacrjournals.org.
Janna Dejmek, et al; "Expression and Signaling Activity of Wnt-5a/Discoidin Domain Receptor-1 and Syk Plays Distinct but Decisive Roles in Breat Cancer Patient Survival", Clinical Cancer Research, vol. 11, Jan. 15, 2005, pp. 520-528.
Claudia K. Derian, et al "Selective Inhibition of N-Formylpeptide-Induced Neutrophil Activation by Carbamate-Modified Peptide Analogues", Biochemistry, 1996, 35(4), 1265-1269; Downloaded from http://pubs.acs.org on Jan. 26, 2009.
Samudra K. Dissanayake, et al; "The Wnt5A/Protein Kinase C Pathway Mediates Motility in Melanoma Cells via the Inhibition of metastasis Suppressors and Initiation of an Epithelial to Mesenchymal Transition", Published in final edited form as: J. Biol Chem. Jun. 8, 2007; 282(23): 17259-17271.
Valérie Gouon, et al; "UP-Regulated Expression of the β3 Integrin and the 92-kDA Gelatinase in Human HT-144 Melanoma Cell Tumors Grown in Nude Mice", Int. J. Cancer; vol. 68, Issue 5, pp. 650-662, Nov. 27, 1996.
Keith S. Hoek, et al; "Metastatic potential of melanomas defined by specific gene expression profiles with no BRAF signature", Pigment Cell Res. vol. 19, Issue 4, pp. 290-302, Aug. 2006; Article first published online: Jun. 23, 2006.
Bassam Janji, et al; "Autocrine TGF-β-Regulated Expression of Adhesion Receptors and Integrin-Linked Kinase in HT-144 Melanoma Cells Correlates With Their Metastatic Phenotype", Int. J. Cancer; vol. 83, Issue 2, pp. 255-262, Oct. 8, 1999.
Eun-Jung Jin, et al; "Wnt-5a is involved in TGF-β3-stimulated chondrogenic differentiation of chick wing bud mesenchymal cells", The International Journal of Biochemistry & Cell Biology, vol. 38, Issue 2, Feb. 2006, pp. 183-195.
Marzieh Jönsson, et al; "Loss of Wnt-5a Protein Is Associated with Early Relapse in Invasive Ductal Breast Carcinomas", Cancer Res 2002; vol. 62, Jan. 15, 2002, pp. 409-416.
N. Kremenevskaja, et al; "Wnt-5a has tumor suppressor activity in thyroid carcinoma", Oncogene, vol. 24, Issue 13, Mar. 24, 2005, pp. 2144-2154.
Manabue Kurayoshi, et al; "Expression of Wnt-5a Is Correlated with Aggressiveness of Gastric Cancer by Stimulating Cell Migration and Invasion" Cancer Res. Nov. 1, 2006, vol. 66, Issue 21, pp. 10439-10448.
Manabu Kurayoshi, et al; "Post-translational palmitoylation and glycosylation of Wnt-5a are necessary for its signaling", Biochem J. 402, pp. 515-523, 2007 (Exact Date Not Given).
Yingying Le, et al; "Formyl-peptide receptors revisited", Trends in Immunology, vol. 23, No. 11, Nov. 2002, pp. 541-548, Published online: Oct. 4, 2002.
Tracey B. Lewis, et al; "Molecular Classification of Melanoma Using Real-Time Quantitative Reverse Transcriptase-Polymerase Chain Reaction", Cancer, vol. 104, Issue 8, pp. 1678-1686, Oct. 15, 2005; Article first published online Aug. 22, 2005.
Huiling Liang, et al; "Wnt5a inhibits B cell proliferation and functions as a tumor suppressor in hematopoietic tissue", Cancer Cell, vol. 4, Issue 5, pp. 349-360, Nov. 1, 2003.

(Continued)

*Primary Examiner* — Elly-Gerald Stoica
(74) *Attorney, Agent, or Firm* — Ladas & Parry LLP

(57) ABSTRACT

The present invention relates to a novel unbranched carbamate derivative, in particular N-butyloxycarbonyl derivative of certain Wnt5-α peptides and to their use in the treatment of melanoma or gastric cancer, as well as a method for treating melanoma as well as a pharmaceutical composition comprising the same derivative.

15 Claims, 8 Drawing Sheets

OTHER PUBLICATIONS

X.H. Liu, et al; "Expression of Wnt-5a and its clinicopathological significance in hepatocellular carcinoma", Digestive and Liver Disease, vol. 40, Issue 7, Jul. 2008, pp. 560-567; Available online Feb. 21, 2008.

Rajbabu Pakala, et al; "Inhibition of Arterial Thrombosis by a Peptide Ligand of the Thrombin Receptor", Thrombosis Research, vol. 100, Issue 1, Oct. 1, 2000, pp. 89-96.

Michael D. Pierschbacher, et al; "Variants of the cell recognition site of fibronectin that retain attachment-promoting activity", Proceedings of the National Academy of Science, vol. 81, No. 19, Oct. 1, 1984, pp. 5985-5988.

Kevin Roarty, et al; "Wnt5a is required for proper mammary gland development and TGF-β-mediated inhibition of ductal growth", Development 134, pp. 3929-3939, Nov. 1, 2007, Published online before print Sep. 26, 2007.

Burkhard Rost; "PHD: Predicting One-Dimensional Protein Structure by Profile-Based Neural Networks", Methods in Enzymology, vol. 266, pp. 525-539, 1996 (Exact Date not Given), available online Dec. 6, 2003.

Tanja Rothhamer, et al; "Bone Morphogenic Proteins are Overexpressed in Malignant Melanoma and Promore Cell Invastion and Migrations", Cancer Res. 2005, 65: pp. 448-456. Published online Feb. 3, 2005.

Annette Säfholm et al; "A Formylated Hexapeptide Ligand Mimics the Ability of Wnt-5a to Impria Migration of Human Breast Epithelial Cells", Journal of Biological Chemistry, vol. 281, No. 5, pp. 274-2749, Feb. 3, 2006.

Malini Sen, et al; "Blockade of Wnt-5A/Frizzled 5 Signaling Inhibits Rheumatoid Synoviocyte Activation", Arthritis & Rheumatism, vol. 44, No. 4, Apr. 2001, pp. 772-781.

Patricia Van Belle, et al; "Melanoma-Associated Expression of Transforming Growth Factor-β Isoforms", American Journal of Pathology, vol. 148, No. 6, Jun. 1996, pp. 1887-1894.

Ashani T. Weeraratna, et al; "Wnt5a signaling directly affects cell motility and invasion of metastatic melanoma", Cancer Cell, Apr. 2002, vol. 1, pp. 279-288.

Manabu Kurayoshi, et al; "Expression of Wnt-5a is Correlated with Aggressiveness of Gastric Cancer by Stimulating Cell Migration and Invasion", Cancer Res. Nov. 1, 2006; 66(21):10439-48.

Claudia K. Derian, et al; "Selective Inhibition of $N$-Formylpeptide-Induced Neutrophil Activation by Carbamate-Modified Peptide Analogues", Biochemistry Jan. 30, 1996; 35(4):1265-9.

Tobias Pukrop, et al; "The complex pathways of Wnt 5a in cancer progression", J. Mol Med. Mar. 2008; 86(3):259-66. Epub Oct. 19, 2007. Review.

Ashani T. Weeraratna, et al; "Wnt5a signaling directly affects cell motility and invasion of metastatic melanoma", Cancer Cell, Apr. 2002; 1:279-288.

International Search Report: PCT/SE2009/050935; mailed Nov. 18, 2009.

International Preliminary Report on Patentability mailed Feb. 24, 2011; International Application No. PCT/SE2009/050935.

European Search Report; Feb. 14, 2012, Appln. EP 09 80 6925.

* cited by examiner

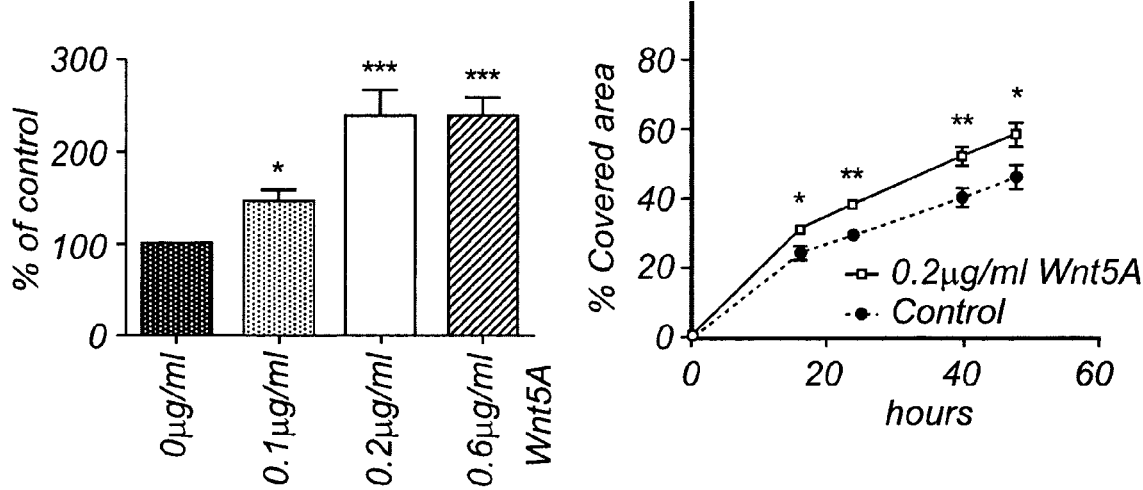
*Fig. 4a*
*Fig. 4b*
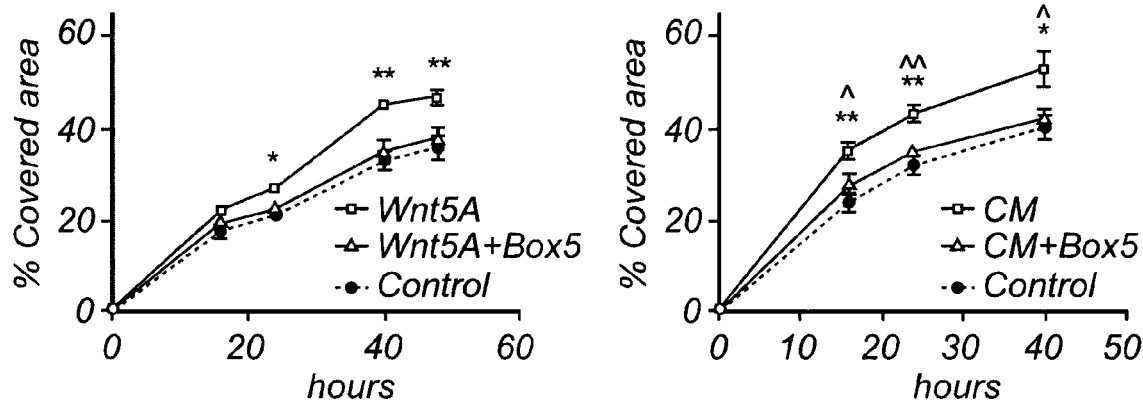
*Fig. 4c*
*Fig. 4d*
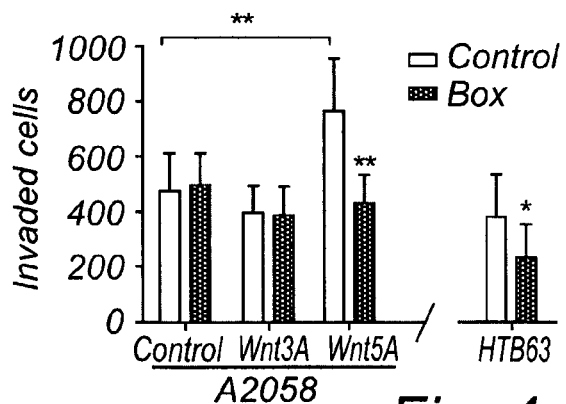
*Fig. 4e*

USE OF WNT5-α PEPTIDE DERIVATES FOR THE TREATMENT OF MELANOMA AND GASTRIC CANCER

TECHNICAL FIELD

The present invention relates to certain unbranched carbamate derivatives of certain Wnt5-α derivatives as well as treatment of melanoma by using these Wnt5-α derivatives.

BACKGROUND OF THE INVENTION

Melanoma is a malignant tumor of melanocytes, which are found predominantly in skin but also in the bowel and the eye. It is one of the rarer types of skin cancer but causes the majority of skin cancer related deaths. Malignant melanoma is a potentially serious type of skin cancer. It is due to uncontrolled growth of pigment cells, called melanocytes. Despite many years of intensive laboratory and clinical research, the sole effective cure is surgical resection of the primary tumor before it achieves a thickness greater than 1 mm.

Around 160,000 new cases of melanoma are diagnosed worldwide each year, and it is more frequent in males and caucasians. It is more common in Caucasian populations living in sunny climates than other groups. According to the WHO Report about 48,000 melanoma related deaths occur worldwide per annum. Malignant melanoma accounts for 75 percent of all deaths associated with skin cancer.

The treatment includes surgical removal of the tumor; adjuvant treatment; chemo- and immunotherapy, or radiation therapy.

The risk for developing melanoma depends on two groups of factors: intrinsic and environmental. "Intrinsic" factors are generally an individual's family history and inherited genotype, while the most relevant environmental factor is sun exposure. Epidemiologic studies suggest that exposure to ultraviolet radiation (UVA and UVB) is one of the major contributors to the development of melanoma. UV radiation causes damage to the DNA of cells, typically thymine demonization, which when unrepaired can create mutations. When the cell divides, these mutations are propagated to new generations of cells. If the mutations occur in oncogenes or tumor suppressor genes, the rate of mitosis in the mutation-bearing cells can become uncontrolled, leading to the formation of a tumor. Occasional extreme sun exposure (resulting in "sunburn") is causally related to melanoma.

Possible significant elements in determining risk include the intensity and duration of sun exposure, the age at which sun exposure occurs, and the degree of skin pigmentation. Exposure during childhood is a more important risk factor than exposure in adulthood. This is seen in migration studies in Australia where people tend to retain the risk profile of their country of birth if they migrate to Australia as an adult. Individuals with blistering or peeling sunburns (especially in the first twenty years of life) have a significantly greater risk for melanoma. This does not mean that sunburn is the cause of melanoma. Instead it is merely statistically correlated. The cause is the exaggerated UV-exposure. It has been shown that sunscreen—while preventing the sunburn—does not protect from melanoma. Many researchers say that sunscreen can even increase the melanoma risk. Fair and red-headed people, persons with multiple atypical nevi or dysplastic nevi and persons born with giant congenital melanocytic nevi are at increased risk.

The incidence of melanoma has increased in the recent years, but it is not clear to what extent changes in behavior, in the environment, or in early detection are involved.

To understand how sunscreen can reduce sunburn and at the same time cause melanoma it is necessary to distinguish between direct DNA damage and indirect DNA damage. Genetic analysis has shown that 92% of all melanoma are caused by the indirect DNA damage. Familial melanoma is genetically heterogeneous, and loci for familial melanoma have been identified on the chromosome arms 1p, 9p and 12q.

The signs and symptoms of melanoma are:
asymmetrical skin lesion.
lesion border is irregular.
melanomas usually have multiple colors.
moles greater than 5 mm are more likely to be melanomas than smaller moles.
The evolution (i.e. change) of a mole or lesion may be a hint that the lesion is becoming malignant.

The most common types of melanoma in the skin are:
superficial spreading melanoma (SSM)
nodular melanoma
acral lentiginous melanoma
lentigo maligna (melanoma)

Any of the above types may produce melanin (and be dark in colour) or not (and be amelanotic—not dark). Similarly any subtype may show desmoplasia (dense fibrous reaction with neurotropism) which is a marker of aggressive behaviour and a tendency to local recurrence.

Elsewhere:
clear cell sarcoma (melanoma of soft parts)
mucosal melanoma
uveal melanoma Features that affect prognosis are tumor thickness in millimeters (Breslow's depth), depth related to skin structures (Clark level), type of melanoma, presence of ulceration, presence of lymphatic/perineural invasion, presence of tumor infiltrating lymphocytes (if present, prognosis is better), location of lesion, presence of satellite lesions, and presence of regional or distant metastasis.

Certain types of melanoma have worse prognoses but this is explained by their thickness. Interestingly, less invasive melanomas even with lymph node metastases carry a better prognosis than deep melanomas without regional metastasis at time of staging. Local recurrences tend to behave similarly to a primary unless they are at the site of a wide local excision (as opposed to a staged excision or punch/shave excision) since these recurrences tend to indicate lymphatic invasion.

When melanomas have spread to the lymph nodes, one of the most important factors is the number of nodes with malignancy. Extent of malignancy within a node is also important; micro metastases in which malignancy is only microscopic have a more favorable prognosis than macro metastases. In some cases micro metastases may only be detected by special staining, and if malignancy is only detectable by a rarely-employed test known as polymerase chain reaction (PCR), the prognosis is better. Macro metastases in which malignancy is clinically apparent (in some cases cancer completely replaces a node) have a far worse prognosis, and if nodes are matted or if there is extra capsular extension, the prognosis is still worse.

When there is distant metastasis, the cancer is generally considered incurable. The five year survival rate is less than 10%. The median survival is 6 to 12 months. Treatment is palliative, focusing on life-extension and quality of life. In some cases, patients may live many months or even years with metastatic melanoma (depending on the aggressiveness of the treatment). Metastases to skin and lungs have a better prognosis. Metastases to brain, bone and liver are associated with a worse prognosis.

Melanoma appears in different stages, which are denoted Stage 0, which is melanoma in situ having 100% survival, Stage I/II, which invasive melanoma having 85-95% survival, Stage II, which is high risk melanoma having 40-85% survival, Stage III which is regional metastasis having 25-60% survival, Stage IV, which is distant metastasis having 9-15% survival based upon AJCC 5-year survival with proper treatment.

Surgery is the first choice therapy for localized cutaneous melanoma. Depending on the stage a sentinel lymph node biopsy is done as well, although controversy exists around trial evidence for this procedure. Treatment of advanced malignant melanoma is performed from a multidisciplinary approach.

High risk melanomas may require adjuvant treatment. In the United States most patients in otherwise good health will begin up to a year of high-dose interferon treatment, which has severe side effects but may improve the patient's prognosis. This claim is not supported by all research at this time, and in Europe interferon is usually not used outside the scope of clinical trials.

Various chemotherapy agents are used, including dacarbazine (also termed DTIC), immunotherapy (with interleukin-2 (IL-2) or interferon (IFN)) as well as local perfusion are used by different centers. They can occasionally show dramatic success, but the overall success in metastatic melanoma is quite limited. IL-2 (Proleukin®) is the first new therapy approved for the treatment of metastatic melanoma in 20 years. Studies have demonstrated that IL-2 offers the possibility of a complete and long-lasting remission in this disease, although only in a small percentage of patients. A number of new agents and novel approaches are under evaluation and show promise.

Radiation therapy is often used after surgical resection for patients with locally or regionally advanced melanoma or for patients with unresectable distant metastases. It may reduce the rate of local recurrence but does not prolong survival.

The molecular background of melanoma progression has been extensively studied and gene expression analysis has identified several genes differentially expressed in invasive forms of melanoma versus less invasive melanoma or benign nevi, one such gene is Wnt-5a (Bittner et al., 2000). Wnt-5a is a secreted, cystein-rich protein that undergoes posttranslational glycosylation and lipid modifications (Kurayoshi et al., 2007). Following its secretion, Wnt-5a acts in an auto- or paracrine fashion by binding to its receptor, in malignant melanoma Wnt-5a has been shown to bind the G-protein coupled receptor Frizzled-5 (Weeraratna, 2002). It is considered as a non-canonical Wnt protein, indicating that it does not primarily act via the β-catenin signaling pathway. The importance of Wnt-5a in cancer progression has been studied in different types of cancer during the last years. Wnt-5a has been shown to have tumour suppressor activity in breast cancer, thyroid cancer, lymphoma, neuroblastoma, colon cancer and liver cancer (Jönsson 2002; Kremenevskaja 2005: Liang 2003; Blanc 2005; Dejmek 2005; Liu 2008). However, in other types of cancer like malignant melanoma and gastric cancer an increased expression of Wnt-5a has been shown to promote tumour progression (Bittner et al., 2000, Weeraratna, 2002; Lewis et al., 2005; Kurayoshi et al., 2006). Based on these results one can conclude that in certain cancers a substance mimicking the effects of Wnt-5a might serve to inhibit tumour progression (Säfholm, 2006) whereas in other cancers, like malignant melanoma, an inhibitor of Wnt-5a-mediated tumour progression would be required.

Regarding the functional downstream effects of Wnt-5a protein in malignant melanoma, only limited knowledge is available (Weeraratna et al., 2002; Dissanayake et al., 2007).

In cells derived from melanoma tissue samples an increased expression of the Wnt-5a protein has been shown to induce increased cell adhesion, migration and invasion. In the same study the authors also showed that the effects of Wnt-5a were mediated via the Frizzled-5 receptor and a downstream protein kinase C (PKC) signal (Weeraratna et al., 2002). In a more recent paper, the authors further show that Wnt-5a induces epithelial-mesenchymal transition (EMT) via a PKC-induced expression of Snail that leads to a decrease in the level of E-cadherin but an increase in the level of vimentin (Dissanayake et al., 2007). However, the question still remains as to the actual cause of the increased expression of Wnt-5a in malignant melanomas.

In a recent study by Hoek and co-workers based on DNA microarray analysis it was suggested that transforming growth factor-β (TGF-β) plays a decisive role in the regulation of Wnt-5a gene expression (Hoek et al., 2006). Interestingly enough, members of the TGF-β superfamily (Van Belle et al., 1996) and the bone morphogenic protein (BMP; Rothhammer et al., 2005) exhibit an increased expression in malignant melanoma. Furthermore, at least some functional effects of TGF-β also overlap with that of Wnt-5a. More specifically, as previously mentioned for Wnt-5a, TGF-β1 induces EMT and an increase in melanoma cell migration and metastatic potential (Janji et al., 1999; Gouon et al., 1996. Finally, both Wnt-5a- and TGF-β1 mediate changes in the cellular protein levels of E-cadherin, certain integrins and matrix metalloproteinases (Dissanayake et al., 2007; Janji et al., 1999). There are publications from non-cancer systems that have demonstrated a direct link between TGF-β signaling and Wnt-5a expression. For example, in chick wing bud mesenchymal cells TGF-β3 has been shown to increase Wnt-5a expression resulting in PKCα activation and chondrogenic differentiation (Jin et al., 2006). In a more recent publication in mice, TGF-β1 was shown to increase Wnt-5a expression in mammary epithelial cells leading to inhibition of ductal extension and lateral branching in the developing mammary gland (Roarty and Serra, 2007). Consequently, inhibition of TGF-β signaling could potentially be an attractive mechanism whereby Wnt-5a mediated tumour cell migration and metastasis could be impaired.

SUMMARY OF THE INVENTION

The present invention relates to a Wnt5-α derivative to be used in the treatment of melanoma and gastric cancer as well as a method for treating melanoma and gastric cancer.

DETAILED DESCRIPTION OF THE PRESENT INVENTION

In particular the invention relates to unbranched carbamate derivatives, in particular N-butoxycarbonyl derivatives of certain Wnt5-α peptides, and more particularly to an unbranched carbamate derivative, in particular N-butoxycarbonyl derivative of one or more of the peptides

| | |
|---|---|
| MDGCEL | SEQ. ID. NO: 1 |
| GMDGCEL | SEQ. ID. NO: NO: 2 |
| EGMDGCEL | SEQ. ID. NO: NO: 3 |
| SEGMDGCEL | SEQ. ID. NO: 4 |
| TSEGMDGCEL | SEQ. ID. NO: 5 |

-continued

```
KTSEGMDGCEL          SEQ. ID. NO: 6
NKTSEGMDGCEL         SEQ. ID. NO: 7
CNKTSEGMDGCEL        SEQ. ID. NO: 8
LCNKTSEGMDGCEL       SEQ. ID. NO: 9
RLCNKTSEGMDGCEL      SEQ. ID. NO: 10
GRLCNKTSEGMDGCEL     SEQ. ID. NO: 11
QGRLCNKTSEGMDGCEL    SEQ. ID. NO: 12
TQGRLCNKTSEGMDGCEL   SEQ. ID. NO: 13
GTQGRLCNKTSEGMDGCEL  SEQ. ID. NO: 14
LGTQGRLCNKTSEGMDGCEL SEQ. ID. NO: 15
```

A further aspect of the invention relates to an unbranched carbamate derivatives, in particular N-butoxycarbonyl derivate of the above peptides for use in the treatment of melanoma and gastric cancer.

A further aspect of the invention relates to a pharmaceutical composition containing at least one unbranched carbamate derivatives, in particular N-butoxycarbonyl derivate of the above peptides for use in the treatment of melanoma and gastric cancer.

In a preferred embodiment thereof the pharmaceutical composition is a topical composition.

A further aspect of the invention relates to a method for treating melanoma by administering a therapeutically effective amount of an unbranched carbamate derivative, in particular N-butoxycarbonyl derivate of the above peptides to a subject suffering from melanoma and gastric cancer.

A further aspect of the invention relates to a method for prophylactic treatment of melanoma by administering a therapeutically effective amount of unbranched carbamate derivative, in particular N-butoxycarbonyl derivate of the above peptides to a subject being in the risk zone for obtaining melanoma and gastric cancer.

The term unbranched carbamate derivated herein means one of the derivatives of the group N-methyloxycarbonyl, N-ethyloxycarbonyl, N-n-propyloxycarbonyl or N-butyloxycarbonyl derivative, whereby the latter may be preferred.

The present invention will be described in the following by reference to some experiments carried out.

A) Analysis of the absence or presence of Wnt-5a, Frizzled-2 and Frizzled-5 mRNA in A2058 and HTB63 melanoma cells. The human breast cancer cell line MCF-7 (M) served as a positive control for all of these transcripts and β-actin as loading control. Plus (+RT) and minus (−RT) indicate reactions performed with and without reverse transcriptase. For Fzd2 and Fzd5, the PCR reactions are performed on 3.5 times the amount of cDNA used for the β-actin control.

B) To further characterize the presence of Wnt-5a transcript in HTB63 cells the inventor also determined by Western blot the cellular levels of Wnt-5a protein in A2058 and HTB63 cells using recombinant Wnt-5a (rW5a) as a positive control and β-actin as loading control. The inventor also performed Western blot analysis of serum-free culture medium collected from A2058 and cells after 48 hours to reveal the absence or presence of secreted Wnt-5a protein from these cells. Recombinant Wnt-5a protein served as a positive control. Each of the outlined results was repeated as independent experiments at least three times.

FIG. 2 illustrates Foxy5 which is a Wnt-5a agonist in melanoma cells. A shows the Foxy5 structure (formyl group marked). B shows that Foxy5 (50 μM) promotes A2058 cell migration (wound-healing assay) over a time-course consisting of 0, 16, 24, 40 and 48 hours. Error bars represent s.e.m. Paird-t-tests; *$p<0.05$.

Figure 3:
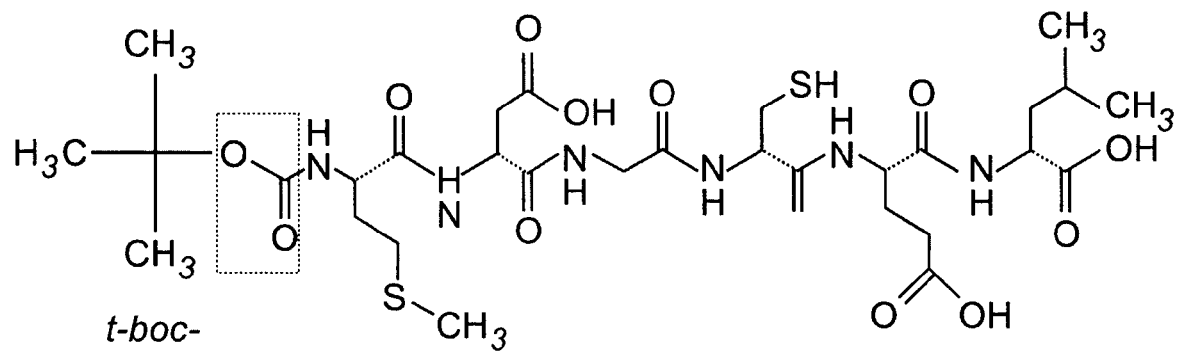

FIG. 3 shows the structure of Box5, which is a modified analogue of Foxy5.

FIG. 4 illustrates the effects of Wnt-5a and a novel N-butyloxycarbonyl hexapeptide, Box5, on melanoma cell adhesion and migration.

A) A2058 melanoma cells were stimulated with the indicated concentrations of Wnt-5a, detached with Versene and resuspended as single cells in serum-free medium in the presence or absence of recombinant Wnt-5a at the indicated concentrations. Cells were then allowed to adhere in a 96-well plate. After a period of 60 min the non-adherent cells were washed away while the adherent cells were stained and their number determined. This number is presented as a percentage of the control (no Wnt-5a) stimulation B) A2058 melanoma cells were cultured to confluence in a 12-well plate after which a scratch was inflicted in each well, the medium was changed to fresh serum-free medium lacking (closed circles) or containing 0.2 μg/ml Wnt-5a (open squares).

C) A2058 melanoma cells were cultured to confluence in a 12-well plate after which a scratch was inflicted to each well, the medium was changed to fresh serum-free medium in the absence of any additive (closed circle), the presence of 0.2 μg/ml Wnt-5a alone (open squares) or the presence of 0.2 μg/ml Wnt-5a with 100 μM Box5 (open triangle).

D) HTB63 melanoma cells were cultured to confluence in a 12-well dish after which a scratch was inflicted to each well, the medium was changed to fresh serum-free medium (closed circle), conditioned medium (open squares) or conditioned medium supplemented with 100 μM Box5 (open triangle). To record changes in migration in panels B-D, a picture was taken from each scratch/well from the same area of cells after 0, 16, 24, 40 or 48 hours, and the wound-healing was expressed as percentage of wound area closed.

E) Prior to the initiation of each experiment, the A2058 cells (the six bars to the left) and the HTB63 cells (the two bars to the right) were detached with Versene and resuspended as single cells in serum-free medium. The cells were pre-incubated for 40 min with continuous agitation in the absence (open bars) or presence (solid bars) of 100 μM Box5. An aliquot of the cell suspension containing 25,000 cells was then added to the upper Transwell chamber, and the lower chamber was filled with serum-containing (10%) medium. As indicated 0.1 μg/ml Wnt-3a, 0.2 μg/ml Wnt-5a and/or 100 μM Box5 were added to the upper chamber. The cells were then allowed to invade for 24 hours after which the attached cells on the lower side of the membrane were counted. The results in are given as means±SEM (n=5-7). *=$p<0.05$, =$p<0.01$, and *=$p<0.001$ where values are compared to the control. (FIG. 5D, CM vs. CM+Box5, ^=$p<0.05$, ^^=$p<0.01$, and ^^^=$p<0.001$).

FIG. 5 illustrates that Box5 has no effect on the basal migration of A2058 melanoma cells, but can inhibit TGFβ1 induced migration. A) Wound healing analysis of A2058 cells in the presence (□) or absence (●) of 100 μM Box5. B) Wound healing assay of A2058 cells pre-incubated with or without 100 μM of Box5 for 40 minutes, and then further stimulated with or without 5 ng/ml TGFβ1 as indicated. All wound healing data is expressed as percentage of the wound area closed after 0, 16, 40 and 48 hours.

Figure 6A:
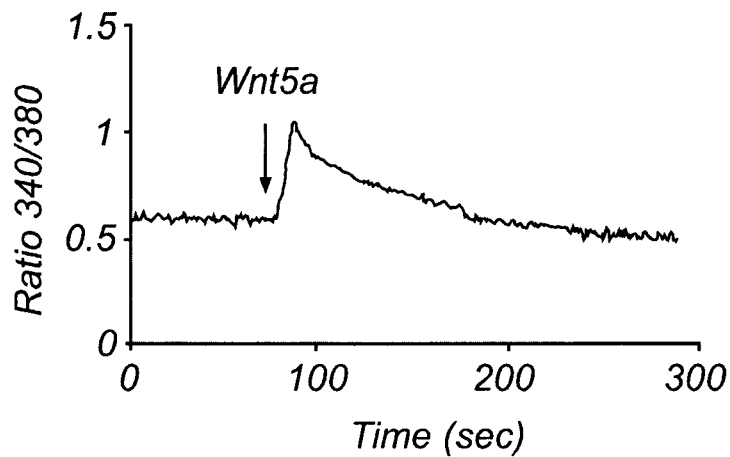

FIG. 6 illustrates that the Wnt-5a/$Ca^{2+}$ signalling pathway is essential for Wnt-5a mediated melanoma cell invasion. A) rWnt-5a (0.1 μg/l; addition indicated by arrow) triggers a rapid cytosolic $Ca^{2+}$ signal in A2058 cells. B) pre-incubation of A2058 cells with 10 μM MAPT/AM for 30 minutes abolishes rWnt-5a (0.1 μg/ml) stimulation (indicated by arrow) of cytosolic $Ca^{2+}$. C) MAPT/AM abolishes Wnt-5a induced A2058 cell invasion. Cells were pre-incubated with 10 μM MAPT/AM for 30 minutes, then stimulated with/without rWnt-5a (0.2 μg/l), and then with 1 μM MAPT/AM throughout the duration of the invasion experiment (24 hours), where the latter treatment condition had the same chelating effect on $Ca^{2+}$ as 10 μM of MAPT/AM for 30 minutes, shown in FIG. 6A. Error bars represent s.e.m. Paired t-tests; *$p<0.05$, *** $p<0.001$.

FIG. 7 illustrates the effect of Box5 on Wnt-5a-induced $Ca^{2+}$ signaling and PKC activation.

Figure 8A:
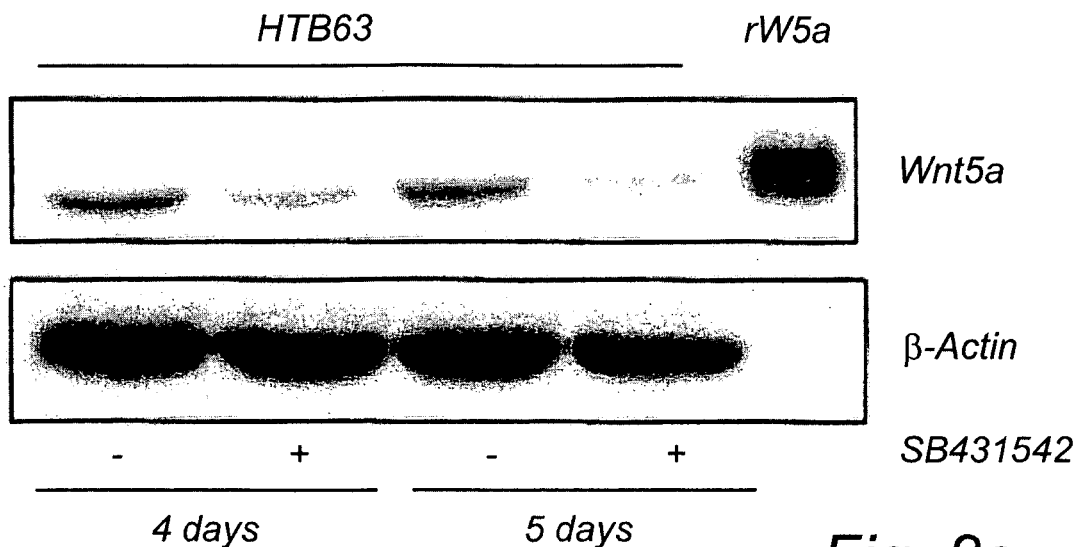

The fluorescence signals from fura-2 loaded A2058 melanoma cells, pre-incubated (overnight) and incubated in the absence or presence of Box5 (100 μM), were recorded following stimulation with either Wnt-5a (0.1 μg/ml), endothelin-1 (ET-1)(10 nM) or charbacol (5 μM). A) Representative $Ca^{2+}$ traces from A2058 cells stimulated with Wnt-5a, endothelin-1 or charbacol, the latter two being G-protein receptor ligand controls. B) Two $Ca^{2+}$ traces from A2058 melanoma cells pre-incubated and incubated with Box5 and then stimulated with Wnt-5a (first arrow) and then again with either endothelin-1 (second arrow top trace) or charbacol (second arrow in lower trace). All traces shown are representative of at least five separate experiments. C) The accumulated results of $\Delta Ca^{2+}$ changes in ratio values (basal level to peak level) recorded from A2058 cells stimulated with Wnt-5a, endothelin-1 or charbacol in the absence (open bars) or presence of Box5 (solid bars) are show. D) pre-incubation with Box5 (100 μM) overnight inhibits MARCKS phosphorylation after 45 minutes or rWnt-5a stimulation (0.2 μg/ml). 1 nM PMA was used as a positive indicatior for MARCHS phosphorylation. The results in are given as means±SEM, ***=$p<0.001$ FIG. 8 illustrates the effects of TGF-β1 signaling on Wnt-5a protein expression in A2058 and HTB63 melanoma cells.

A) Representative Western blot showing the effects of incubating HTB63 melanoma cells in the absence or presence of the selective TGF-β1 receptor antagonist SB431542 (10 μM) for 4 or 5 days on their endogenous Wnt-5a expression. Recombinant Wnt-5a served as a positive control and β-actin as loading control.

B) Western blots showing the effects of 24 hours stimulation with increasing concentrations of TGF-β1 on Wnt-5a expression in A2058 cells. Recombinant Wnt-5a served as a positive control and β-actin as loading control. C) Western blots showing the effects of stimulation with 5 ng/ml of TGF-β1 for increasing periods of time on Wnt-5a expression in A2058 cells. Recombinant Wnt-5a served as a positive control and β-actin as loading control. Each of the outlined results was repeated as independent experiments at least four times.

FIG. 9 illustrates the effects of TGF-β1 and Box5 on melanoma cell adhesion and migration.

A) A2058 melanoma cells were stimulated with the indicated concentrations of TGF-β1, detached with Versene and re-suspended as single cells in serum-free medium. The cells were then allowed to adhere in a 96-well plate and following a period of 60 min non-adherent cells were washed away while the adherent cells were stained and their number determined. This number is presented as a percentage of the control (no TGF-β1 stimulation B) HTB63 melanoma cells were cultured to confluence in a 12-well dish after which a scratch was made in each well, the medium changed to a fresh serum-free medium in the absence (closed circle) or presence of 10 μM SB431542 (open square).

C) A2058 melanoma cells were cultured to confluence in a 12-well dish after which a scratch was inflicted to each well, the medium was changed to a fresh serum-free medium in the absence of any additive (closed circle) or the presence of 5 ng/ml TGF-β1 alone (open square) or the presence of 5 ng/ml TGF-β1 with 100 μM Box5 (open triangle). In the experiments outlined in panels B and C a picture was taken from each scratch/well from the same area of cells after 0, 16, 24, 40 or 48 hours, and the wound-healing was expressed as percentage of wound area closed.

D) Prior to the initiation of each experiment, the A2058 cells (the two bars to the left) and the HTB63 cells (the two bars to the right) were detached with Versene and re-suspended as single cells in serum-free RPMI medium. An aliquot of the cell suspension containing 25,000 cells was then added to the upper Transwell chamber, and the lower chamber was filled with serum-containing (10%) medium. As indicated, the cells were allowed to invade in the absence (open bars) or presence of either 5 ng/ml TGF-β1 (solid bar) or 10 μM SB431542 (solid bar) in the upper chamber. The cells were then allowed to invade for 24 hours after which the attached cells on the lower side of the membrane were counted.

The results in are given as means±SEM (n=5-10). *= $p<0.05$, =$p<0.01$, and *=$p<0.001$

EXPERIMENTALS

Antibodies and Peptides

The following primary antibodies were used: β-actin monoclonal AC-15 Ab (Sigma Aldrich, St. Louis, Mo.); TGF-β1 chicken polyclonal Ab (R&D Systems Europe Ltd., Abingdon, UK). The polyclonal antibody towards Wnt-5a was produced in the inventor's laboratory against amino acids 275-290 of the mature Wnt-5a molecule, as previously described (Jonsson et al., 2002). The secondary peroxidase-conjugated anti-chicken IgY (IgG) whole molecule was from Sigma Aldrich (St. Louis, Mo.); all other peroxidase-conjugated IgGs were obtained from Dakopatts (Glostrup, Denmark). Inbiolabs Ltd (Tallinn, Estonia) synthesized the novel Wnt-5a-derived N-butyloxycarbonyl hexapeptide (Met-Asp-Gly-Cys-Glu-Leu; Box5) on two different occasions. The two batches of Box5 peptide had similar results in the inventor's assays. The synthesized batches of Box5 peptide (>95% pure) were quality controlled by RP-HPLC and mass spectrometry. The formylated control peptide used: formyl-Nle-Leu-Phe-Nle-Tyr-Lys was from Sigma-Aldrich (St. Louis, Mo.). Chemicals—Benzamidine, bovine serum, all types of tissue culture media were from Sigma-Aldrich (St. Louis, Mo.). The human recombinant Wnt-5a, Wnt-3a and TGF-β1 proteins were purchased from R&D Systems Europe Ltd. (Abingdon, UK). Human Porcine endothelin-1 and charbacol were purchased from Sigma Aldrich (St. Louis, Mo.). The protease inhibitors pefabloc, leupeptin, and aprotinin were from Roche Molecular Biochemicals (Mannheim, Germany). The selective inhibitor of the TGF-β type I receptor activin receptor-like kinase ALK5 and its relatives ALK4 and 7 SB431542 (Inman et al., 2002) was purchased from Tocris Bioscience (Tocris Cookson Ltd., Bristol, UK). Enhanced chemiluminescence (ECL) detection reagents were purchased from Santa Cruz Biotechnology, Inc. (Stockholm, Sweden) whereas all other electrophoresis reagents came from BioRad (Richmond, Calif.). All other chemicals were of analytical grade and were purchased from Sigma-Aldrich (St. Louis, Mo.).

Cell Culture

The human malignant melanoma cell line A2058 was a generous gift of László Kopper from the Department of Pathology and Experimental Cancer Research, Semmelweis University, Budapest, Hungary. The A2058 cells were maintained in RPMI 1640 supplemented with 10% FBS, 5 U/ml penicillin, 0.5 U/ml streptomycin, and 2 mM glutamine.

The HTB63 (also referred to as HT144) human malignant melanoma cell line was purchased from the American Type Culture Collection (ATCC; LGC Promochem AB, Boras, Sweden) and maintained in McCoy's 5A medium supplemented with 10% FBS, 5 U/ml penicillin, 0.5 U/ml streptomycin, and 2 mM glutamine.

The human mammary breast carcinoma cells, MCF7 (positive control for Wnt-5a expression), were grown in DMEM supplemented with 10% FBS, 5 U/ml penicillin, 0.5 U/ml streptomycin, and 2 mM glutamine. All cell cultures were maintained at 37° C. in a humidified atmosphere of 5% carbon dioxide.

Western Blot

The cells were either directly lysed in 1× Laemmli buffer containing DTT and boiled for 10 min, or lysed in buffer containing 50 mM Tris-HCl (pH 7.5), 1% Triton X-100, 100 mM NaCl, 10 mM $MgCl_2$, 20% glycerol, 1 mM $Na_3VO_4$, and protease inhibitors (20 μg/ml aprotinin, 1 μg/ml leupeptin, 2.5 mM benzamidine, and 2 mM pefabloc). Cell treated with lysis buffer were centrifuged at 15,000 rpm for 5 min at 4° C. The protein content in each sample was determined and adjusted to ensure equal loading of protein in each lane. Thereafter, 50 mM DTT and 5× concentrated Laemmli buffer was added and the samples boiled for 5 min. The samples were separated by SDS polyacrylamide gel electrophoresis and subsequently transferred to PVDF membranes. For immunoblotting the membranes were blocked in PBS supplemented with 0.2% Tween 20 and 1% non-fat milk for Wnt-5a or 3% non-fat milk as for all other antibodies for 1 h. Thereafter the membranes were incubated for 1 h at room temperature or overnight at 4° C. with the indicated primary Ab (1:25,000 for β-actin; 1:1, 000 for Wnt-5a and 1:1,000 for TGF-β1) in 2% non-fat milk or 1.5% BSA. After extensive washing in PBS with 0.2% Tween, the membranes were incubated for 1 h with a horseradish peroxidase-conjugated secondary Ab in 2% non-fat milk or 1.5% BSA and again extensively washed. Finally, the Ab-antigen complexes were detected using enhanced chemiluminescence. For re-probing, the membranes were stripped with a Reblot Strong solution from Chemicon International (Temecula, Calif.). The Western blots shown are representative of at least three independent experiments.

RT-PCR

RNA extraction was carried out using TRIzol® from Invitrogen ( ) according to the manufacturer's instructions. The RNA concentration was measured using a Nanodrop Spectrophotometer ND-1000 (Bio-Rad (Hercules Calif.). Prior to reverse transcription, the RNA was treated with 1 U/μl DNaseI (Invitrogen). cDNA was synthesised, using random hexamers from Fermentas (Helsingborg, Sweden), 1-2 μg of total RNA using M-MuLV RT (Fermentas, Helsingborg, Sweden). PCR reactions in a 50 μl volume used 5 μl of RT reaction in 1× Taq polymerase buffer (75 mM Tris-HCl, 20 mM $[NH4]_2SO_4$, 0.01% Tween 20), with the addition of 2.5 mM $MgCl_2$, 200 mM dNTPs, 1 μM of each primer and 1 unit of Taq DNA polymerase (Fermentas, Helsingborg, Sweden).

Figure 1A:
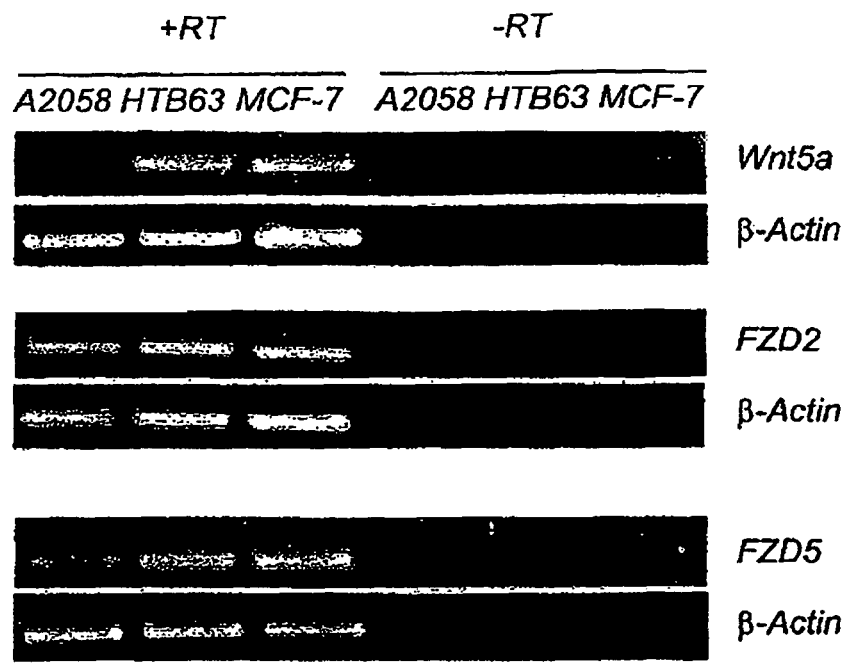
FIG. 1 illustrates characterization of the A2058 and HTB63 melanoma cell lines.

PCR primers were as follows: Wnt-5a forward: 5'-GGATTGTTAAACTCAACTCTC-3' (SEQ. ID. NO: 16); Wnt-5a reverse: 5'-ACACCTCTTTCCAAACAGGCC-3' (SEQ. ID. NO: 17); β-actin forward: 5'-TTCAACACCCCAGCCATGTA-3' (SEQ. ID. NO: 18); β-actin reverse: 5'-TTGCCAATGGTGATGACCTG-3' (SEQ. ID. NO: 19); Frizzled-2 forward: 5'-ACATCGCCTACAACCAGACC-3' (SEQ. ID. NO: 20) and Frizzled-2 reverse: 5'-CTCGCCCAGAAACTTGTAGC-3' (SEQ. ID. NO: 21); Frizzled-5 forward: 5'-ACACCCGCTCTACAACAAGG-3' (SEQ. ID. NO: 22) and Frizzled-5 reverse: 5'-CGTAGTGGATGTGGTTGTGC-3' (SEQ. ID. NO: 23). The RT-PCRs shown in FIG. 1 are representative of at least three independent experiments Cell Adhesion Cells pre-treated and stimulated as described below were detached with Versene, re-suspended in serum-free RPMI medium and samples containing 30,000 cells from each treatment group were added to each well of a 96-well plate The cells were allowed to adhere for 60 min at 37° C. in a humidified atmosphere of 5% carbon dioxide after which the non-adherent cells were washed away with PBS. The adherent cells were fixed in 1% glutaraldehyde for 10 min at room temperature and then stained with 0.5% crystal violet in 20% methanol for 10 min. Finally, the stain from each group of cells was dissolved in 50% acetic acid. The amount of dissolved stain from each well was thereafter measured in a Fluostar plate reader (BMG Lab Technologies GmbH, Offenberg, Germany) at 544 nm. The individual samples from each separate experiment were analysed in quadruplicate and the accumulated data were based on 5 separate experiments. The results are illustrated in FIG. 4.

A) A2058 melanoma cells were stimulated with the indicated concentrations of Wnt-5a, detached with Versene and resuspended as single cells in serum-free medium in the presence or absence of recombinant Wnt-5a at the indicated concentrations. Cells were then allowed to adhere in a 96-well plate. After a period of 60 min the non-adherent cells were washed away while the adherent cells were stained and their number determined. This number is presented as a percentage of the control (no Wnt-5a) stimulation (FIG. 4A)

B) A2058 melanoma cells were cultured to confluence in a 12-well plate after which a scratch was inflicted in each well, the medium was changed to fresh serum-free medium lacking (closed circles) or containing 0.2 μg/ml Wnt-5a (open squares). (FIG. 4B)

C) A2058 melanoma cells were cultured to confluence in a 12-well plate after which a scratch was inflicted to each well, the medium was changed to fresh serum-free medium in the absence of any additive (closed circle), the presence of 0.2 μg/ml Wnt-5a alone (open squares) or the presence of 0.2 μg/ml Wnt-5a with 100 μM Box5 (open triangle). (FIG. 4C)

D) HTB63 melanoma cells were cultured to confluence in a 12-well dish after which a scratch was inflicted to each well, the medium was changed to fresh serum-free medium (closed circle), conditioned medium (open squares) or conditioned medium supplemented with 100 μM Box5 (open triangle). To record changes in migration in panels B-D, a picture was taken from each scratch/well from the same area of cells after 0, 16, 24, 40 or 48 hours, and the wound-healing was expressed as percentage of wound area closed. (FIG. 4D)

E) Prior to the initiation of each experiment, the A2058 cells (the six bars to the left) and the HTB63 cells (the two bars to the right) were detached with Versene and resuspended as single cells in serum-free medium. The cells were pre-incubated for 40 min with continuous agitation in the absence (open bars) or presence (solid bars) of 100 μM Box5. An aliquot of the cell suspension containing 25,000 cells was then added to the upper Transwell chamber, and the lower chamber was filled with serum-containing (10%) medium. As indicated 0.1 μg/ml Wnt-3a, 0.2 μg/ml Wnt-5a and/or 100 μM Box5 were added to the upper chamber. The cells were then allowed to invade for 24 hours after which the attached cells on the lower side of the membrane were counted. The results in are given as means±SEM (n=5-7). *= $p<0.05$, = $p<0.01$, and *= $p<0.001$ where values are compared to the control. (FIG. 4D, CM vs. CM+Box5, ^= $p<0.05$, ^^= $p<0.01$, and ^^^= $p<0.001$).

Wound Healing Assay

Cells were plated in 12 well plates and allowed to grow into a confluent layer in complete RPMI (for A2058 cells) or complete McCoy's 5A medium (for HTB63 cells). As indicated, cells were pre-incubated with the Box5 peptide (100 μM) or control solvent for 40 min with continuous agitation. A wound was then inflicted by making a scratch through the confluent layer of cells with a pipette tip. During the migration period of the assay, cells were incubated either in serum-free medium or in the case of HTB63 cells in their own serum-free-conditioned medium collected from cells cultured for 48 h and used within 2 days after collection. The exact conditions of each experiment are described above. To avoid loss of activity, cell medium was changed after 24 hours. A picture for each scratch was taken in the same area of cells at 0, 16, 24, 40 and 48 hours, and wound healing was measured as percentage of wound area closed. For each experimental condition wound healing was analysed in triplicate. All data were based on 3 to 8 separate experiments as indicated.

Cell Invasion

Cell invasion was analyzed using the BD Matrigel™ invasion chamber assay (BD Biosciences, Bedford, Mass.). Prior to the initiation of each experiment, the cells were detached with Versene and re-suspended as single cells in serum-free RPMI medium. As indicated, cells were pre-incubated with the Box5 peptide (100 μM) or control solvent for 40 min with continuous agitation. An aliquot of the cell suspension containing 25,000 cells and 100 μM Box5 or control solvent was then added to the upper transwell chamber, and the lower chamber was filled with serum-containing (10%) medium. Simultaneously, Wnt-5a, Wnt-3a or the TGF-β1 inhibitor SB431542 were added to the upper chamber as indicated in FIG. 7. The invasion chambers were shaken horizontally for 5 min to ensure even distribution of the cells in suspension and subsequently across the membrane surface. The cells were allowed to invade for the periods of time indicated at 37° C. in a humidified atmosphere of 5% $CO_2$. The medium was discarded and cells were fixed in 4% paraformaldehyde for 10 min. The cells were stained with 0.5% crystal violet in 20% methanol for 10 min and the non-invading cells on the inner side of the membrane were removed with a cotton-tipped applicator. The membrane was cut out of the chamber using a scalpel blade and the stained cells on the lower chamber side of the membrane were counted.

Determination of Cytosolic Free Calcium Levels

Figure 1B:

Cells grown on a glass cover slip were incubated with 4 μM fura-2/AM in culture medium for 30 minutes at 37° C. (Dejmek et al., 2006). After fura-2 loading of the cells, the cover slips were washed and mounted in a specially designed chamber to which was added a calcium-containing medium (136 mM NaCl, 4.7 mM KCl, 1.2 mM $MgSO_4$, 1.1 mM $CaCl_2$, 1.2 $KH_2PO_4$, 5 mM $NaHCO_3$, 5.5 mM glucose and 20 mM Hepes, pH 7.4). The chamber was then placed in a system consisting of a NIKON Diaphot microscope connected to a Photon Technology International (PTI) imaging system. The cells were first allowed to rest for 10 minutes before any stimulation was performed. Fura-2 fluorescence was then recorded continuously from the cells before and after the stimulations with either Wnt-5a, endothelin-1 or charbacol (as indicated in the legend to FIG. 8) using an excitation wavelength rapidly alternating between 340 and 380 nm, while the emission wavelength was set at 510 nm. The fluorescence intensity ratios (340/380 nm) were subsequently calculated and analyzed using the PTI Image Master Software. Statistical analysis—The Student's t-test for unpaired samples was used to analyze differences in the experiments, where *= $p<0.05$, = $p<0.01$, and *= $p<0.001$ Characterization of the A2058 and HTB63 Melanoma Cell Lines To further investigate the effects of Wnt-5a expression and signaling in melanoma cells it was decided to use two different human melanoma cell lines, A2058 and HTB63. Both A2058 and HTB62 melanoma cells express Frizzled-5 receptors (FIG. 1A), the proposed Wnt-5a receptor in melanoma cells (Weeraratna 2002). In contrast, a much weaker expression of Frizzled-2 receptors was observed in cell lines. Further characterization revealed that A2058 cells lack an endogenous expression of Wnt-5a mRNA and protein, whereas HTB63 cells, in contrast, exhibit a solid endogenous expression of Wnt-5a mRNA (FIG. 1A) and protein (FIG. 1B).

In order to ascertain that the endogenous Wnt-5a expressed in HTB63 cells is indeed secreted, the media in which the cells were grown was analyzed by Western-blot for the presence of Wnt-5a. The lower blot in FIG. 1B clearly reveals that HTB63 cells not only express but also secretes Wnt-5a. Wnt-5a and Frizzled-5 expressing MCF-7 breast cancer cells and recombinant Wnt-5a were used as positive controls in these experiments. These data suggest that the expression of Wnt-5a in these cell lines is regulated at the transcriptional level, which is in contrast to breast cancer tissue and cells where it is regulated at the translational level (Dejmek, Leandersson). To date the factors that regulate Wnt-5a transcription in melanoma cells are unknown.

Development of a Wnt-5a Antagonist Peptide

Figure 2A:
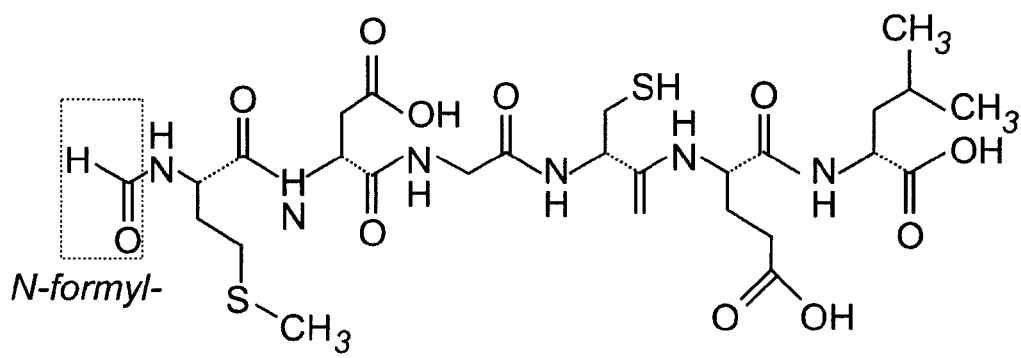
Figure 2B:
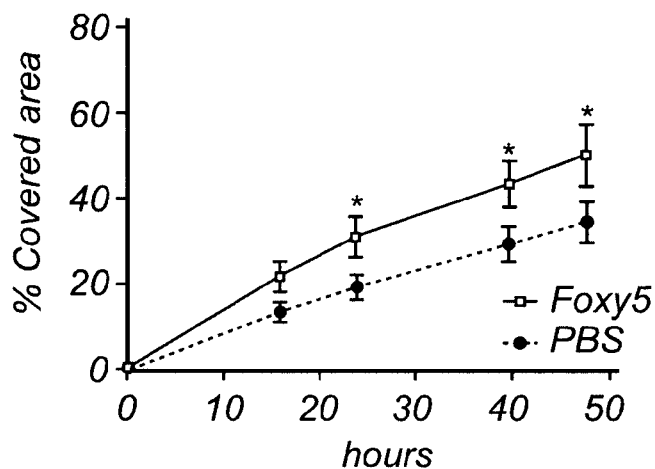

Previously, the inventor has identified a Wnt-5a derived, N-formulated hexapeptide (Foxy5; FIG. 2A) that functions as an agonist of Wnt-5a signalling. This peptide mimics the effects of Wnt-5a in breast cancer cell lines, and possesses anti-tumorgenic functions in vivo. It was found that Foxy5 could also mimic the pro-migratory effects of Wnt-5a in A2058 melanoma cells (FIG. 2B) suggesting this peptide functions as a Wnt-5a agonist in diverse cell types. Interestingly, it has previously been shown that specific modification of a formylated bacterially-derived chemotactic peptide (formyl-Met-Leu-Phe), converted the molecule from an agonist to an antagonist analogue. It has now been shown that such a modification of Foxy5 could also change its Wnt-5a agonist functions to that of an antagonist. This t-boc-Met-Asp-Gly-Cys-Glu-Leu peptide has been termed Box5 (FIG. 3)

Figure 5A:
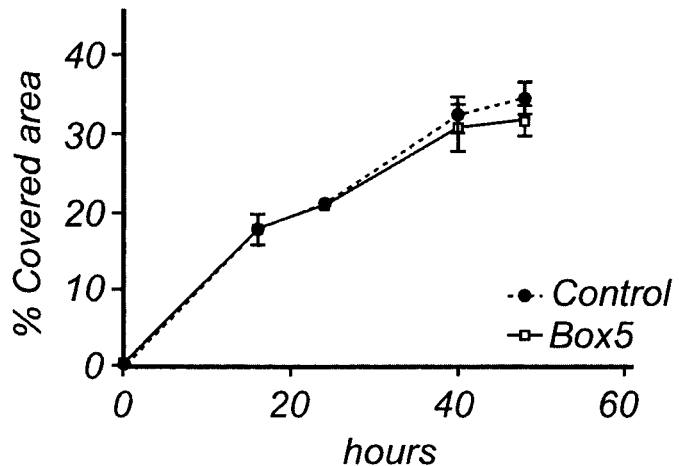
Figure 5B:
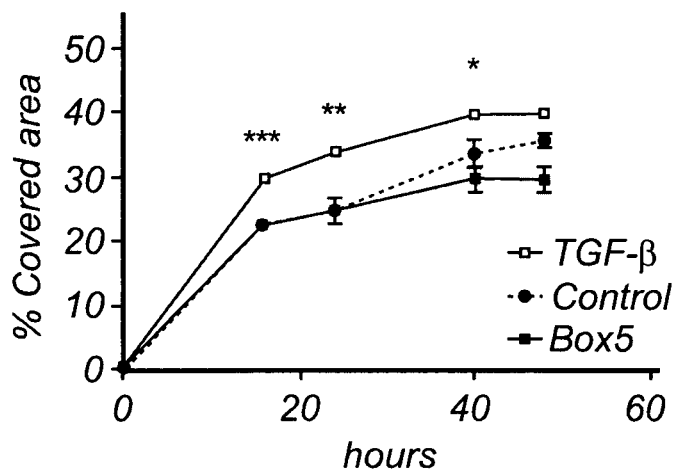

Effects of Wnt-5a and the N-Butyloxycarbonyl Hexapeptide Box5 on Cell Adhesion and Migration The effects of Wnt-5a were tested on the adhesion of A2058 melanoma cells. Wnt-5a enhanced the adhesive capacity of the A2058 melanoma cells and a maximal effect was obtained following stimulation with 0.2 μg/ml (FIG. 4A). Based on these findings it was then explored how this concentration of recombinant Wnt-5a affected the migration of A2058 cells in a wound-healing assay. The results outlined in FIG. 4B clearly show that addition of Wnt-5a (0.2 µg/ml) at the start of the experiments increased the migration of A2058 melanoma cells. To specifically inhibit this Wnt-5a induced migration of melanoma cells it was subsequently developed and tested a novel and N-butyloxycarbonyl modified peptide. It has previously been shown that a Wnt-5a-derived formylated hexapeptide can mimic the inhibitory effect of Wnt-5a on breast cancer cell migration in vitro (Säfholm 2006) and that this peptide also inhibits breast cancer metastasis in a mouse model (Säfholm, 2008). Here it was tested the possibility of adding a butyloxycarbonyl group to the N-terminal methionine residue of the hexapeptide to gain an inhibitor of Wnt-5a signaling. The basis for this manipulation is the finding that such a modification of a bacterial-derived chemotactic peptide (formyl-Met-Leu-Phe) has been reported to change the action of the peptide from an agonist to an antagonist (Derian, 1996). The ability of this butyloxycarbonyl modified hexapeptide, hereafter referred to as Box5, was tested to inhibit the migration of both A2058 and HTB63 melanoma cells in a wound-healing assay. Box5 abolished the Wnt-5a-induced migration of A2058 cells (FIG. 4C), but had no effect on the intrinsic migration of those cells that lack endogenous expression (FIG. 5A). It was also shown that TGF1β mediated migration of A2058 cells could be blocked by pre-incubation with Box5 (FIG. 5B) These data are also supported by the findings that Box5, but not a formylated control hexapeptide (data not shown), inhibits the migration of HTB63 cells to the same extent as a change of the conditioned media (containing secreted Wnt-5a) to a fresh serum-free media (lacking Wnt-5a) (FIG. 4D). The wound-healing assay investigates migration of cells present in a monolayer that are characterized by numerous cell-cell interactions. However, it does not reflect the in vivo situation where tumor cells are forced to invade the extra-cellular matrix and therefore it was next performed similar experiments in an invasion assay.

During the metastatic process tumour cells need to invade into the extracellular matrix, so the efficacy of Box5 to block cell invasion in a 3-dimensional cell culture model was tested. Addition of Box5 abolished Wnt-5a induced invasion of A2058 cells, an effect not seen when the cells were stimulated with the canonical Wnt ligand, Wnt-3a (FIG. 4E). Box5 also had the ability to inhibit invasion of HTB63 cells, by antagonising the effects of endogenous Wnt-5a (FIG. 4E). Collectively these data show that Box5 is a potent antagonist of Wnt-5a mediated migration and invasion of melanoma cells, both of which are essential components of the metastatic process.

The results obtained in the wound-healing assay were confirmed in the invasion assay with regard to the ability of Wnt-5a to stimulate the invasion of A2058 melanoma cells. Furthermore, this effect of Wnt-5a on melanoma cell invasion was not seen when the cells were stimulated with the canonical ligand Wnt-3a. Again, addition of the Box5 peptide abolished the Wnt-5a-induced invasion of A2058 melanoma cells but had no effect on their basal invasion. In addition, Box5 could also inhibit the invasion of HTB63 melanoma cells that had an endogenous expression and secretion of Wnt-5a.

Figure 6B:
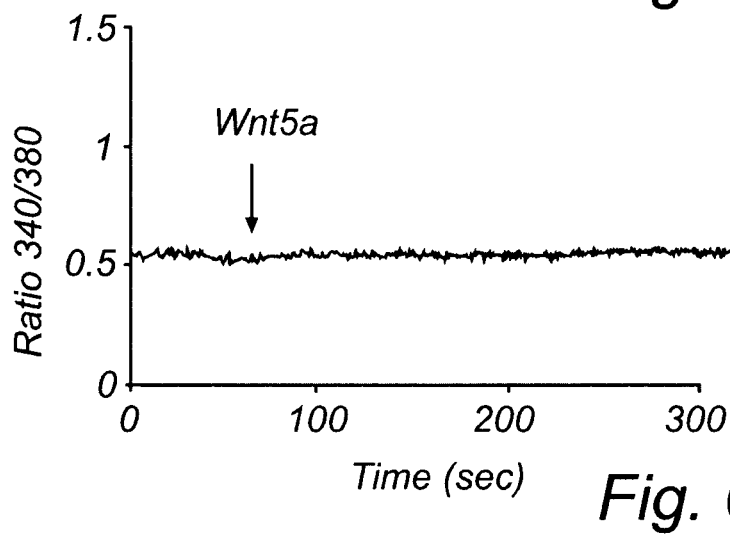

The Wnt/Ca2+ Signalling Pathway is Essential for Wnt-5a Mediated Melanoma Cell Invasion To identify the molecular basis for the antagonistic functions of Box5, the signalling pathways that are essential for Wnt-5a induced melanoma cell invasion was investigated. It was found that Wnt-5a stimulates a rapid cytosolic $Ca^{2+}$ signal in A2058 cells (FIG. 6A), which can be inhibited by using the intracellular $Ca^{2+}$ chelator MAPT/AM (FIG. 6B).

Figure 6C:
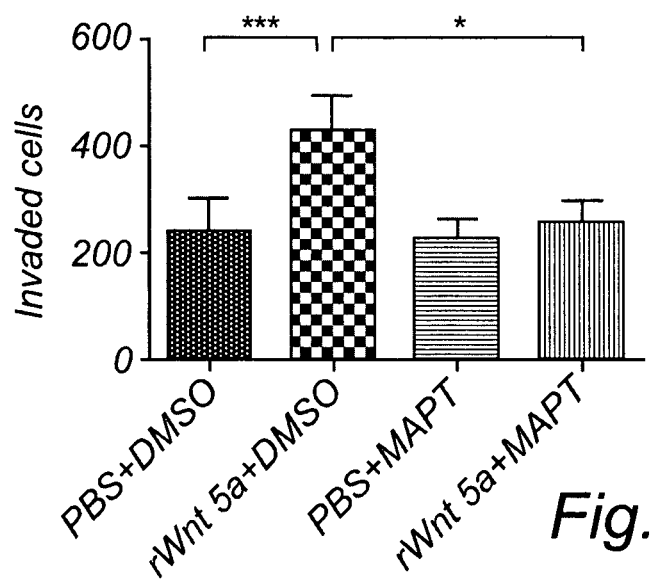

MAPT/AM $Ca^{2+}$ chelation was used to assess the invasive capacity of melanoma cells in the absence of Wnt-5a $Ca^{2+}$ induced signalling. The pro-invasive effect of Wnt-5a on the A2058 cells was completely abolished by MAPT/AM (FIG. 6C). This demonstrated that the $Ca^{2+}$ signalling component of Wnt-5a stimulation is essential for mediating melanoma cell invasion.

Effects of the N-Butyloxycarbonyl Hexapeptide Box5 on Wnt-5a-Induced Signaling

Figure 7A:
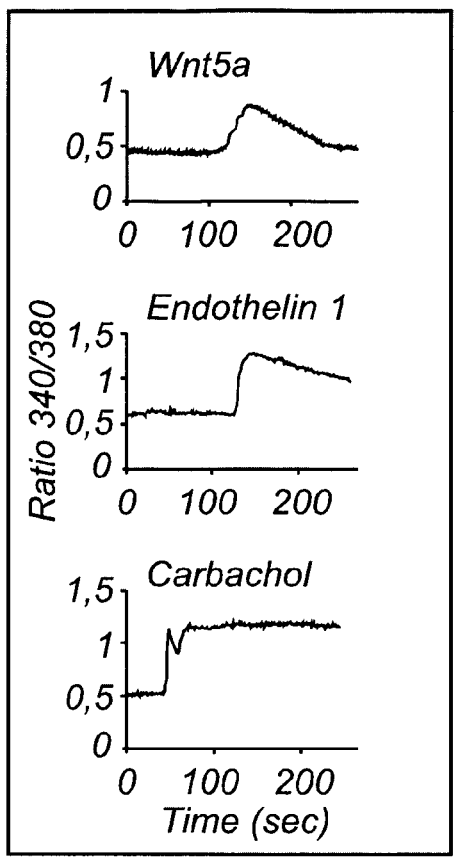

To further investigate the properties of the Box5 hexapeptide and its selective interaction with Wnt-5a receptors, its effects on immediate Wnt-5a-induced receptor signaling was analyzed. Wnt-5a has previously been shown to trigger a prompt increase in cytosolic free $Ca^{2+}$ in thyroid cells (Kremenevskaja, 2005) and in breast cancer cells (Dejmek, 2006). The data show that Wnt-5a also triggers a rapid cytosolic $Ca^{2+}$ signal in A2058 melanoma cells (FIG. 7A) similar to the prompt responses induced by two other G-protein coupled control receptor ligands, endothelin-1 and carbachol (FIG. 7A). It should be noted that in order to obtain approximately similar $Ca^{2+}$ responses for all three ligands, the Wnt-5a concentration was reduced from 0.2 to 0.1 µg/ml in this series of experiments.

Figure 7B:
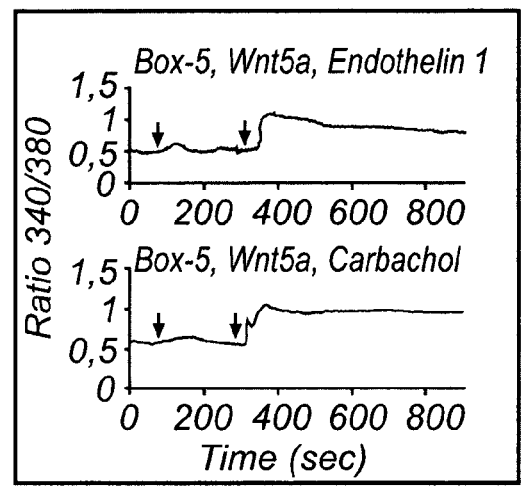
Figure 7C:
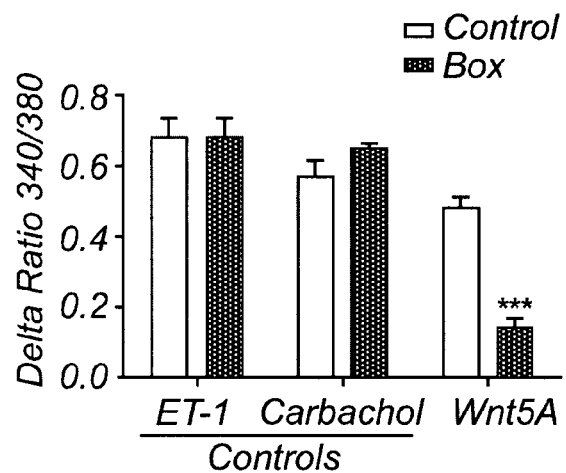

The effects of Box5 was then tested on cells that were first stimulated with Wnt-5a and subsequently with either endothelin-1 or charbacol (FIG. 7B). These experiments reveal that Box5 selectively inhibits the Wnt-5a—but not the endothelin-1 or the charbacol-induced intracellular $Ca^{2+}$ signal in A2058 melanoma cells. Accumulated results on how Box5 affects the Wnt-5a-induced $Ca^{2+}$ signal revealed that there is more than 70% inhibition when compared to the peak values of the $Ca^{2+}$ signal in the absence of Box5 (FIG. 7C). Similar $Ca^{2+}$ experiments in which the cells were stimulated with either endothelin-1 or charbacol in the absence of presence of Box5 revealed no significant effect of this peptide on $Ca^{2+}$ signaling (FIG. 7C).

Figure 7D:
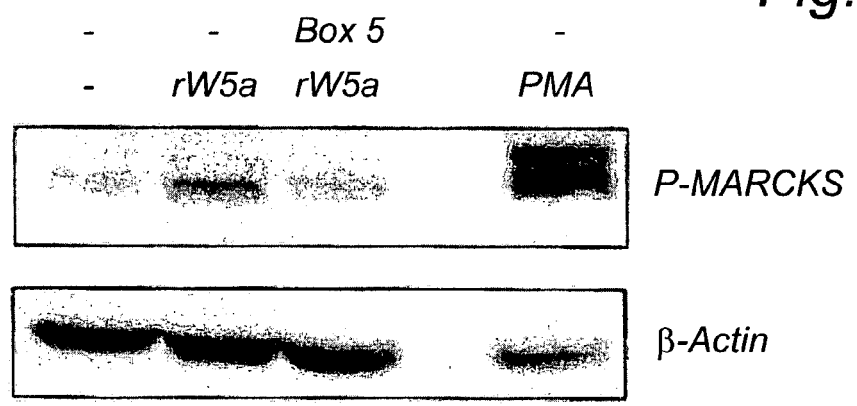

One of the downstream effects of Wnt-5a signalling in melanoma cells is PKC activation. Wnt-5a stimulation of A2050 cells resulted in increased phosphorylation of MARCKS, and endogenous PKC substrated, which was inhibited in the presence of the Box5 peptide (FIG. 7D). These data suggest that Box5 functions to block melanoma cell invasion by directly antagonising Wnt-5a stimulated $Ca^{2+}$ and PKC signalling, resulting in downstream inhibition of Wnt-5a mediated cell invasion.

Although, recording changes of intracellular $Ca^{2+}$ is a very sensitive assay to study modulation of G-protein coupled receptor signaling, it has not been directly related to melanoma cell motility. However, previous studies have demonstrated a downstream effect of Wnt-5a-induced PKC activation on the regulation of melanoma cell migration (Weeraratna et al., 2002, Dissanayake et al., 2007).

Figure 8B:
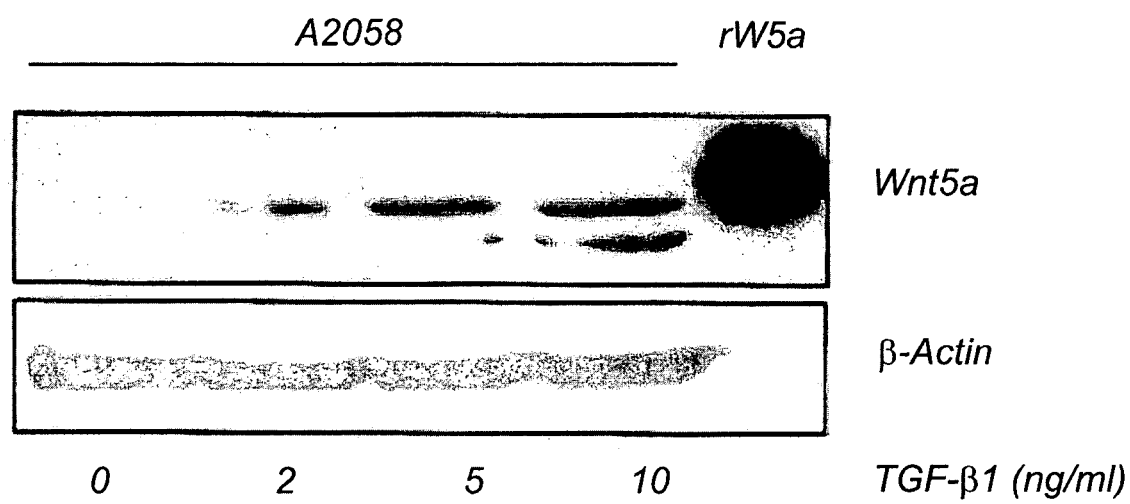
Figure 8C:
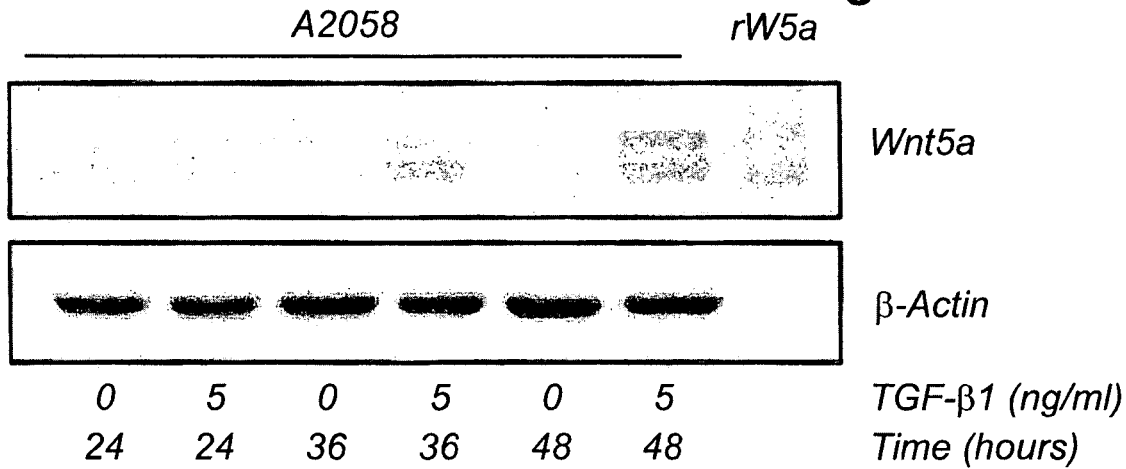

In the present study the level of PKC auto-phosphorylation (Weeraratna et al., 2002, Dissanayake et al., 2007) was not estimated since its relation to PKC kinase activity is unclear. Instead the effects of Wnt-5a and Box5 on the phosphorylation of the endogenous PKC substrate MARCKS were analyzed as a direct means of estimating the activity level of PKC in the melanoma cells. Wnt-5a stimulation of A2058 melanoma cells results in a distinct increase in MARCKS phosphorylation peaking at 9 to 15 min (FIG. 7A). This effect of Wnt-5a was abolished by the Box5 peptide (FIG. 7B). These results again confirm the selective effect of Box5 on melanoma cell migration and invasion (FIGS. 4C-D) and further support the hypothesis that Box5 is a Wnt-5a selective peptide antagonist Effects of SB431542 and TGF-β1 on Wnt-5a Protein Expression in HTB63 and A2058 Cells At present the regulation of Wnt-5a transcription in melanoma cells is unclear. In other cell types, most recently demonstrated in ductal mammary epithelial cells during development (Roarty and Serra, 2007) it was found that TGF-β1 was responsible for regulating Wnt-5a expression at the transcriptional level. In order to explore the possibility that a similar mechanism exists in melanoma cells, the ability of the selective TGF-β1 type I receptor inhibitor SB431542 and recombinant TGF-β1 to affect Wnt-5a expression in the cells was directly tested. The data outlined in FIG. 7C show that when HTB63 cells (that have an endogenous Wnt-5a expression) were kept in complete McCoy's 5A medium supplemented with 10 μM SB431542 for 4-5 days the endogenous Wnt-5a protein expression was significantly reduced after 4 days of incubation and almost abolished after 5 days of incubation. Stimulating A2058 cells (that lack endogenous Wnt-5a expression) for 36 h with different concentrations of recombinant TGF-β1 resulted in an increased expression of Wnt-5a protein (FIG. 8B). These data reveal that a near maximal Wnt-5a expression is achieved upon stimulation with 5 ng/ml of TGF-β1 (FIG. 8B) and that stimulating A2058 cells with 5 ng/ml TGF-β1 required 36 h of stimulation to result in a clearly detectable increase in Wnt-5a protein expression (FIG. 8C). These results confirm that TGF-β1 regulates Wnt-5a expression at least in the two malignant melanoma cell lines used in this study. This raises the possibility that Wnt-5a-mediated melanoma cell migration could be antagonized indirectly by blocking TGF-β1 signaling in these cells.

Figure 9A:
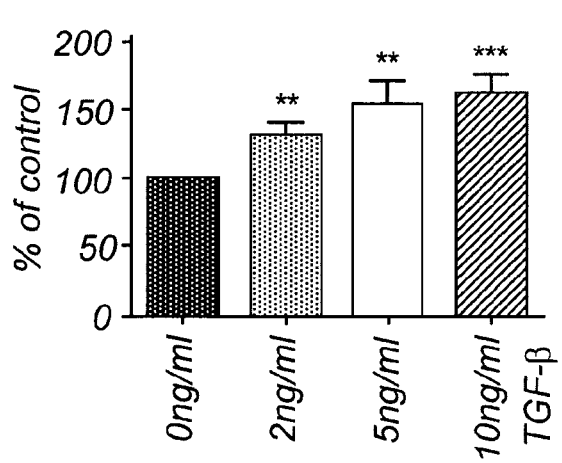
Figure 9B:
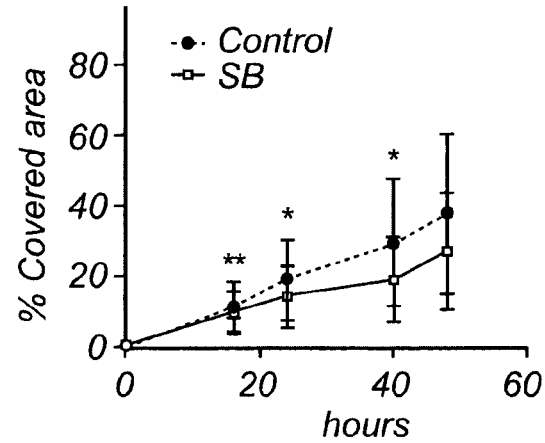
Figure 9C:
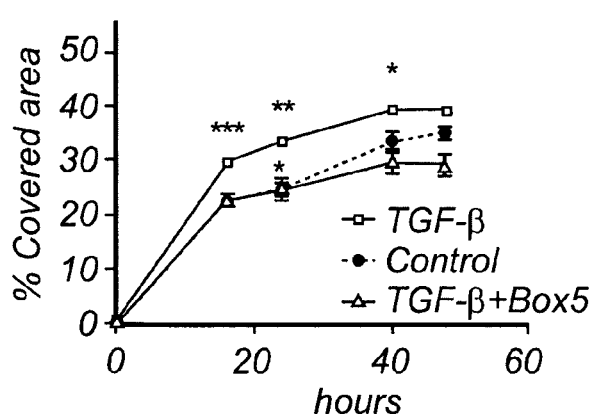
Figure 9D:
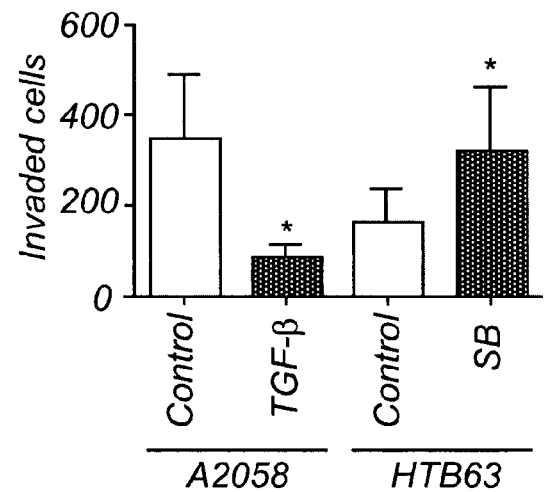

Effects of TGF-β1, SB431542 and Box5 on Melanoma Cell Adhesion, Migration and Invasion To explore whether Wnt-5a indeed is a downstream regulator of TGF-β1-induced cell migration, the effects of TGF-β1 was first tested on the adhesion of A2058 melanoma cells. It was found that TGF-β1 stimulated the adhesive capacity of the A2058 melanoma cells and that the maximal effect was obtained following stimulation with 5 ng/ml (FIG. 9A). Based on these findings it was then explored how this concentration of recombinant TGF-β1 affected the migration of A2058 cells in a wound-healing assay. The results outlined in FIG. 9B clearly shows that addition TGF-β1 (5 ng/ml) at the start of the experiments increased the migration of A2058 melanoma cells. In good agreement with these results it was found that 10 μM SB431542, an inhibitor of the TGF-β type I receptor, inhibited the migration of HTB63 cells (FIG. 9C). Next the ability of Box5 to inhibit the migration of A2058 in a wound-healing assay was tested. Box5 abolished the TGF-β1-induced migration in the two dimensional wound-healing assay (FIG. 9D). Box5 had no effect on the basal migration of A2058 melanoma cells (data not shown). However, when the effect of TGF-β1 (5 ng/ml) on the migration in a more complex migration assay was tested contradictory results were obtained. In the invasion assay TGF-β1 inhibited migration of A2058 cells and SB431542 stimulated the migration of HTB63 cells (FIG. 9E). It was therefore concluded that TGF-β1 is an unpredictable target for blocking Wnt-5a-dependent melanoma cell migration presumably due to its multiple downstream effects.

In the present study it has been demonstrated that a modified Wnt-5a-derived hexapeptide Box5 selectively inhibits Wnt-5a-induced signaling in melanoma cells and blocks the Wnt-5a-mediated migration of these cells in both a wound-healing and an invasion assay. The basis for the design of Box5 comes from previous work in which a secondary/solvent accessible surface predictions according to the PHD method (Rost, 1996) was performed, and then screened for Wnt-5a-derived small peptides with abilities to reconstitute the effects of Wnt-5a on breast tumor cells that lacked an endogenous expression of Wnt-5a (Särndahl, 2006). In that study a Met-Asp-Gly-Cys-Glu-Leu hexapeptide was characterized that after formylation of the N-terminal Met, referred to as Foxy5, was able to mimic the effects of Wnt-5a on signaling and inhibition of breast cancer cell migration (Särndahl, 2006). These effects of Foxy5 were lost if the cells were incubated with a previously described (Sen 2001; Weeraratna 2002) blocking anti-Frizzled-5 antibody, suggesting that Foxy5 mediates its effect on breast cancer cell via the G-protein coupled receptor Frizzled-5 (Säfholm 2006). The same Frizzled receptor has been suggested to be responsible for the signaling and functional effects of Wnt-5a on melanoma cells (Weeraratna 2002 and Dissanayake 2007).

There are several examples of peptide ligands that can specifically activate a distinct receptor; these include the tripeptide Arg-Gly-Asp that functions as an integrin receptor ligand (Pierschbacher and Rouslahti, 1984), the two hexapeptides that specifically activate the G-protein-coupled protease-activated receptors 1 and 4 (Andersen, 1999) and the antagonizing septapeptide that binds the G-protein-coupled receptor for thrombin (Pakala 2000). However, for the present study the most interesting peptide ligand is the bacterial-derived formylated-Met-leu-Phe tripeptide that activates leukocytes by binding with high affinity to the G-protein-coupled formyl peptide receptors on these cells (Le, 2002). If the formyl group of this peptide is exchanged with a butyloxycarbonyl group this tripeptide still binds to the same receptor but instead of acting as an agonist this butyloxycarbonylated tripeptide now acts as an antagonist (Derian 1996). The same modification of the Met-Asp-Gly-Cys-Glu-Leu hexapeptide obviously, as shown here, turns it into a Wnt-5a selective antagonist peptide in melanoma cells.

The data clearly show that Wnt-5a signaling consistently stimulates migration in both A2058 and HTB63 melanoma cells whether a wound-healing or an invasion assay are used and that Box5 in all these situations, blocks Wnt-5a-dependent migration of melanoma cells. Despite the present demonstration that TGF-β1 regulates transcription of Wnt-5a in both the A2058 and the HTB63 melanoma cell lines, and that addition of Wnt-5a always stimulates melanoma cell migration, very inconsistent effects were noted when stimulating melanoma cells with TGF-β1. The effects obtained seem to relate to the type of assay used to investigate cell migration. Most likely these different effects of TGF-β1 on melanoma cell migration relates to its well documented multiple effects on tumour cells. It should be noted that in the situations where TGF-β1 stimulated the migration of melanoma cells, Box5 effectively inhibited its effect on migration. Consequently, the data seem to support that direct intervention with Wnt-5a signaling by a compound such as Box5 could be an effective novel therapeutic approach to selectively inhibit malignant melanoma metastasis.

The abbreviations used are:
BMP—bone morphogenic protein;
EMT—epithelial-mesenchimal transition;
PKC—protein kinase C; and
TGF-β—transforming growth factor-β.

Pharmaceutical Formulations

When employed as pharmaceuticals, the compounds of this invention are usually administered in the form of pharmaceutical compositions. These compounds can be administered by a variety of routes including oral, and rectal. These compounds are effective as oral compositions. Such compositions are prepared in a manner well known in the pharmaceutical art and comprise at least one active compound.

This invention also includes pharmaceutical compositions, which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, soft and hard gelatine capsules, suppositories, and packaged powders.

In preparing a formulation, it may be necessary to mill a compound to provide the appropriate particle size prior to combining with the other ingredients. If the compound is substantially insoluble, it ordinarily is milled to a particle size of less than 200 mesh. If the compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatine, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propyl hydroxy-benzoates; sweetening agents; and flavouring agents. The compositions of the invention can be formulated so as to provide quick, sustained or delayed release of the active ingredient after administration to the patient by employing procedures known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with suitable pharmaceutical excipients. Preferably, the compound of Formula (I) above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. For example, when the drug is administered via the oral route, each dosage contains from about 1 mg to about 1000 mg, preferably about 2 mg to about 500 mg, more preferably about 5 mg to about 100 mg, even more preferably about 5 mg to about 60 mg, of the active ingredient. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like. From a principle point of view the formulation should be administered simultaneously with a food intake, and should then be administered in an amount providing a sufficient inhibition of lipids. Thus the body may need some lipids from a nutritional point of view and this may then influence the amount of inhibiting compounds of the invention administered. The effect of the compounds of the invention takes place in the small intestine and thus there is no further effect obtained as such, but of possible metabolites of the compounds.

For preparing solid compositions such as tablets, the principal active ingredient is mixed with a pharmaceutical excipient to form a solid preformulation composition containing a homogeneous mixture of a compound of the present invention. When referring to these pre-formulation compositions as homogeneous, it is meant that the active ingredient is dispersed evenly throughout the composition so that the composition may be readily subdivided into equally effective unit dosage forms such as tablets, pills and capsules. This solid pre-formulation is then subdivided into unit dosage forms of the type described above containing the active ingredient of the present invention.

The tablets, pills or granules of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The tablets, pills or granules of the present invention may be coated with a sustained release coating enabling release at pancreas, where the pancreatic lipase is set free to the intestine. Such a sustained release coating will thus allow for a small release, if any, in the stomach, but allow for total release in the upper part of the small intestine.

For example, a tablet may be prepared by compression or moulding. Compressed tablets may be prepared by compressing in a suitable machine a composition of the invention in a free-flowing form such as powder or granules, optionally mixed with a binder, a lubricant, an inert diluent, and/or a surface active or dispersing agent. Moulded tablets may be made by moulding in a suitable machine, a mixture of the powdered compound moistened with an inert liquid diluent.

In a preferred embodiment, at least one pharmaceutically acceptable excipient is a binder, filler, or a mixture thereof. Suitable excipients include lubricants, disintegrants, and mixtures thereof. Preferred excipients include, but are not limited to, lactose, croscarmellose, microcrystalline cellulose, pre-gelatinised starch, and magnesium stearate.

Binders suitable for preparing dosage formulations of the pharmaceutical compositions of the invention include, but are not limited to, corn starch, potato starch, or other starches, gelatine, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinised starch, hydroxypropyl methyl cellulose, (e.g., Nos. 2208, 2906, 2910), microcrystalline cellulose and mixtures thereof.

Suitable forms of microcrystalline cellulose include, for example, the materials sold as AVICEL-PH-101, AVICEL-PH-103 and AVICEL-PH-105 (available from FMC Corporation, American Viscose Division, of Marcus Hook, Pa.). A particularly suitable binder is a mixture of microcrystalline cellulose and sodium carboxymethyl cellulose sold as AVICEL RC-581 by FMC Corporation.

Examples of suitable fillers for use with the dosage forms of the compounds of the invention include, but are not limited to, talc, calcium carbonate (e.g., granules or powder), microcrystalline cellulose, powdered cellulose, dextrates, kaolin, mannitol, salicylic acid, sorbitol, starch, pre-gelatinised starch, and mixtures thereof.

Typically, from about 50 to about 99 weight percent of a solid dosage form of the invention is binder and/or filler.

Disintegrants are used to cause the tablet to disintegrate when exposed to an aqueous environment. Too much of a disintegrant will produce tablets which may disintegrate in the bottle due to atmospheric moisture; too little may be insufficient for disintegration to occur and may thus alter the rate and extent of release of the compound of the invention from the dosage form. Thus, a sufficient amount of disintegrant that is neither too little nor too much to detrimentally alter the release of the drug should be used to form solid dosage forms of the invention. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant may be used in the pharmaceutical composition.

Suitable disintegrants that may be used to form solid dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinised starch, other starches, clays, other algins, other celluloses, gums and mixtures thereof.

Suitable lubricants for use with solid dosage forms include, but are not limited to, calcium stearate, magnesium stearate, mineral oil, light mineral oil, glycerine, sorbitol, mannitol, polyethylene glycol, other glycols, stearic acid, sodium lauryl sulphate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. A lubricant may optionally be added, typically in an amount of less than about 1 weight percent of the pharmaceutical composition.

Preferably, each solid dosage form contains from about 5 mg to about 3000 mg of the compound of the invention. Preferably, each solid dosage form contains about 5 mg, about 25 mg, about 100 mg, about 200 mg, about 250 mg, or about 500 mg of the compound of the invention. Solid dosage forms suitable for oral administration preferably contain from about 5 mg to about 200 mg the compound of the invention.

The liquid forms in which the novel compositions of the present invention may be incorporated for administration orally include aqueous solutions, suitably flavoured syrups, aqueous, and flavoured emulsions with edible oils such as corn oil, cottonseed oil, sesame oil, coconut oil, or peanut oil, as well as elixirs and similar pharmaceutical vehicles. Liquid formulations may also be used for inhalation administration, where the active component is suspended in a liquid to be administered using a nasal dispenser. Thereby the active compound may be resorbed either by the mucous membranes in the nasal tract or be resorbed by the lungs.

Other nasal administration compositions are present as dry compositions using a propellant gas for driving the dry composition into the nasal tract and/or lungs.

Furthermore, the pharmaceutical compositions containing one or more compound(s) of this invention can be administered in combination any other suitable drug, for example for the treatment of gastro-intestinal disorders. When the combination therapy is employed, the pharmaceutical composition containing the compound(s) of this invention and the second drug may be administered simultaneously, sequentially or separately. Each component used in the combination therapy is employed in an amount sufficient for its intended purpose. For example, the secondary drug is employed in sufficient amounts to effect reduction of symptom in question in vivo.

Preferably, the dose range for compounds of this invention is from about 1 mg to about 1000 mg per dose, more preferably about 2 mg to about 500 mg, even more preferably about 5 mg to about 100 mg, and still more preferably about 5 mg to about 60 mg. Again, the particular dose used will depend on the patient (age, weight, etc.), and the severity of the disease (mild, moderate, severe). Lastly, a pharmaceutical composition containing two active ingredients can also be prepared for administering the drugs simultaneously.

The administration of the present drug(-s) will normally take place in connection with food intake, when lipase-colipase are set free due to digestion and an optimal inhibition will be obtained below duodenum.

EXAMPLES

The following preparations and examples are given to enable those skilled in the art to more clearly understand and to practice the present invention. They should not be considered as limiting the scope of the invention, but merely as being illustrative and representative thereof.

Formulation Examples

Example 1

Hard gelatine capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatine capsules in 340 mg quantities.

Example 2

A tablet Formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Example 3

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120.0 mg |

The active ingredient, starch and cellulose are passed through a NO: 20 mesh U.S. sieve and mixed thoroughly. The solution of polyvinylpyrrolidone is mixed with the resultant powders, which are then passed through a 16 mesh U.S. sieve. The granules so produced are dried at 50 to 60° C., and passed through a 16 mesh U.S. sieve. The sodium carboxymethyl starch, magnesium stearate, and talc, previously passed through a NO: 30 mesh U.S. sieve, are then added to the granules which, after mixing, are compressed on a tablet machine to yield tablets each weighing 120 mg.

Example 4

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a NO: 20 mesh U.S. sieve, and filled into hard gelatine capsules in 150 mg quantities.

Example 5

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a NO: 60 mesh U.S. sieve and suspended in the saturated fatty acid glycerides previously melted using the minimum heat necessary. The mixture is then poured into a suppository mould of nominal 2.0 g capacity and allowed to cool.

Example 6

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavour and Colour | q.s. |
| Purified water to | 5.0 ml |

The active ingredient, sucrose and xanthan gum are blended, passed through a NO: 10 mesh U.S. sieve, and then mixed with a previously made solution of the microcrystalline cellulose and sodium carboxymethyl cellulose in water. The sodium benzoate, flavour, and colour are diluted with some of the water and added with stirring. Sufficient water is then added to produce the required volume.

Example 7

A formulation may be prepared as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a NO: 20 mesh U.S. sieve, and filled into hard gelatine capsules in 425.0 mg quantities.

Other suitable formulations for use in the present invention can be found in Remington's Pharmaceutical Sciences, edited by E. W. Martin (Mack Publishing Company, 18th ed., 1990).

The invention claimed is:

1. A carbamate derivative of a Wnt5-α peptide consisting of 6-20 consecutive amino acid residues from the C-terminal end of the peptide with SEQ. ID. NO: 15.

2. A method for the treatment of a human being suffering from melanoma or gastric cancer wherein a therapeutically active amount of a carbamate derivative of a Wnt5-α peptide consisting of 6-20 consecutive amino acid residues from the C-terminal end of the peptide with SEQ. ID. NO: 15 is administered to said human.

3. A pharmaceutical composition containing a carbamate derivative of a Wnt5-α peptide consisting of 6-20 consecutive amino acid residues from the C-terminal end of the peptide with SEQ. ID. NO: 15, in combination with one or more pharmaceutically acceptable inert excipients and/or adjuvants.

4. A carbamate derivative of a Wnt5-α peptide according to claim 1, wherein said Wnt5-α peptide is selected from the group consisting of the peptide with SEQ. ID. NO: 1, the peptide with SEQ. ID. NO: 2, the peptide with SEQ. ID. NO: 3, the peptide with SEQ. ID. NO: 4, the peptide with SEQ. ID. NO: 5, the peptide with SEQ. ID. NO: 6, the peptide with SEQ. ID. NO: 7, the peptide with SEQ. ID. NO: 8, the peptide with SEQ. ID. NO: 9, the peptide with SEQ. ID. NO: 10, the peptide with SEQ. ID. NO: 11, the peptide with SEQ. ID. NO: 12, the peptide with SEQ. ID. NO: 13, the peptide with SEQ. ID. NO: 14, and the peptide with SEQ. ID. NO: 15.

5. A carbamate derivative according to claim 4, wherein the derivative is selected from the group consisting of N-methyloxycarbonyl derivative, N-ethyloxycarbonyl derivative, N-n-propyloxycarbonyl derivative and N-butyloxycarbonyl derivative.

6. A carbamate derivative of a Wnt5-α peptide according to claim 4 to be used in the treatment of melanoma and gastric cancer.

7. The method of claim 2, wherein said Wnt5-α peptide is selected from the group consisting of the peptide with SEQ. ID. NO: 1, the peptide with SEQ. ID. NO: 2, the peptide with SEQ. ID. NO: 3, the peptide with SEQ. ID. NO: 4, the peptide with SEQ. ID. NO: 5, the peptide with SEQ. ID. NO: 6, the peptide with SEQ. ID. NO: 7, the peptide with SEQ. ID. NO: 8, the peptide with SEQ. ID. NO: 9, the peptide with SEQ. ID. NO: 10, the peptide with SEQ. ID. NO: 11, the peptide with SEQ. ID. NO: 12, the peptide with SEQ. ID. NO: 13, the peptide with SEQ. ID. NO: 14, and the peptide with SEQ. ID. NO: 15.

8. A method according to claim 7, wherein said derivative is selected from the group consisting of N-methyloxycarbonyl derivative, N-ethyloxycarbonyl derivative, N-n-propyloxycarbonyl derivative and N-butyloxycarbonyl derivative.

9. The pharmaceutical composition of claim 3, wherein said Wnt5-α peptide is selected from the group consisting of the peptide with SEQ. ID. NO: 1, the peptide with SEQ. ID. NO: 2, the peptide with SEQ. ID. NO: 3, the peptide with SEQ. ID. NO: 4, the peptide with SEQ. ID. NO: 5, the peptide with SEQ. ID. NO: 6, the peptide with SEQ. ID. NO: 7, the peptide with SEQ. ID. NO: 8, the peptide with SEQ. ID. NO: 9, the peptide with SEQ. ID. NO: 10, the peptide with SEQ. ID. NO: 11, the peptide with SEQ. ID. NO: 12, the peptide with SEQ. ID. NO: 13, the peptide with SEQ. ID. NO: 14, and the peptide with SEQ. ID. NO: 15.

10. A pharmaceutical composition according to claim 9, wherein the unbranched carbamate derivative is one of the group N-methyloxycarbonyl, N-ethyloxycarbonyl, N-n-propyloxycarbonyl or N-butyloxycarbonyl derivative.

11. A pharmaceutical composition according to claim 9, wherein the composition is formulated as a topical composition.

12. A pharmaceutical composition according to claim 9, wherein the composition is formulated as an injectable composition.

13. The unbranched carbamate derivative of claim 4, wherein said carbamate derivative is an N-butyloxycarbonyl derivative of the peptide with SEQ ID NO:1.

14. The method of claim 7, wherein said carbamate derivative is an N-butyloxycarbonyl derivative of the peptide with SEQ ID NO:1.

15. The pharmaceutical composition of claim 9, wherein said carbamate derivative is an N-butyloxycarbonyl derivative of the peptide with SEQ ID NO: 1.

* * * * *

SEQUENCE LISTING

<160> NUMBER OF SEQ ID NOS: 23

<210> SEQ ID NO 1
<211> LENGTH: 6
<212> TYPE: PRT

<213> ORGANISM: Homo sapiens

<400> SEQUENCE: 1

Met Asp Gly Cys Glu Leu
1               5

<210> SEQ ID NO 2
<211> LENGTH: 7
<212> TYPE: PRT
<213> ORGANISM: Homo sapiens

<400> SEQUENCE: 2

Gly Met Asp Gly Cys Glu Leu
1               5

<210> SEQ ID NO 3
<211> LENGTH: 8
<212> TYPE: PRT
<213> ORGANISM: Homo sapiens

<400> SEQUENCE: 3

Glu Gly Met Asp Gly Cys Glu Leu
1               5

<210> SEQ ID NO 4
<211> LENGTH: 9
<212> TYPE: PRT
<213> ORGANISM: Homo sapiens

<400> SEQUENCE: 4

Ser Glu Gly Met Asp Gly Cys Glu Leu
1               5

<210> SEQ ID NO 5
<211> LENGTH: 10
<212> TYPE: PRT
<213> ORGANISM: Homo sapiens

<400> SEQUENCE: 5

Thr Ser Glu Gly Met Asp Gly Cys Glu Leu
1               5                   10

<210> SEQ ID NO 6
<211> LENGTH: 11
<212> TYPE: PRT
<213> ORGANISM: Homo sapiens

<400> SEQUENCE: 6

Lys Thr Ser Glu Gly Met Asp Gly Cys Glu Leu
1               5                   10

<210> SEQ ID NO 7
<211> LENGTH: 12
<212> TYPE: PRT
<213> ORGANISM: Homo sapiens

<400> SEQUENCE: 7

Asn Lys Thr Ser Glu Gly Met Asp Gly Cys Glu Leu
1               5                   10

<210> SEQ ID NO 8
<211> LENGTH: 13
<212> TYPE: PRT
<213> ORGANISM: Homo sapiens

<400> SEQUENCE: 8

Cys Asn Lys Thr Ser Glu Gly Met Asp Gly Cys Glu Leu
1               5                   10

<210> SEQ ID NO 9
<211> LENGTH: 14
<212> TYPE: PRT
<213> ORGANISM: Homo sapiens

<400> SEQUENCE: 9

Leu Cys Asn Lys Thr Ser Glu Gly Met Asp Gly Cys Glu Leu
1               5                   10

<210> SEQ ID NO 10
<211> LENGTH: 15
<212> TYPE: PRT
<213> ORGANISM: Homo sapiens

<400> SEQUENCE: 10

Arg Leu Cys Asn Lys Thr Ser Glu Gly Met Asp Gly Cys Glu Leu
1               5                   10                  15

<210> SEQ ID NO 11
<211> LENGTH: 16
<212> TYPE: PRT
<213> ORGANISM: Homo sapiens

<400> SEQUENCE: 11

Gly Arg Leu Cys Asn Lys Thr Ser Glu Gly Met Asp Gly Cys Glu Leu
1               5                   10                  15

<210> SEQ ID NO 12
<211> LENGTH: 17
<212> TYPE: PRT
<213> ORGANISM: Homo sapiens

<400> SEQUENCE: 12

Gln Gly Arg Leu Cys Asn Lys Thr Ser Glu Gly Met Asp Gly Cys Glu
1               5                   10                  15

Leu

<210> SEQ ID NO 13
<211> LENGTH: 18
<212> TYPE: PRT
<213> ORGANISM: Homo sapiens

<400> SEQUENCE: 13

Thr Gln Gly Arg Leu Cys Asn Lys Thr Ser Glu Gly Met Asp Gly Cys
1               5                   10                  15

Glu Leu

<210> SEQ ID NO 14
<211> LENGTH: 19
<212> TYPE: PRT
<213> ORGANISM: Homo sapiens

<400> SEQUENCE: 14

Gly Thr Gln Gly Arg Leu Cys Asn Lys Thr Ser Glu Gly Met Asp Gly
1               5                   10                  15

Cys Glu Leu

<210> SEQ ID NO 15
<211> LENGTH: 20
<212> TYPE: PRT

-continued

<213> ORGANISM: Homo sapiens

<400> SEQUENCE: 15

Leu Gly Thr Gln Gly Arg Leu Cys Asn Lys Thr Ser Glu Gly Met Asp
1               5                   10                  15

Gly Cys Glu Leu
            20

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
ggattgttaa actcaactct c                                         21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
acacctcttt ccaaacaggc c                                         21

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ttcaacaccc cagccatgta                                           20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ttgccaatgg tgatgacctg                                           20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
acatcgccta caaccagacc                                           20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21

-continued

```
<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22 acaccgctc tacaacaagg                                               20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
cgtagtggat gtggttgtgc                                              20
```